US010288863B2

(12) United States Patent
Werley et al.

(10) Patent No.: US 10,288,863 B2
(45) Date of Patent: May 14, 2019

(54) OPTOGENETICS MICROSCOPE

(71) Applicant: Q-STATE BIOSCIENCES, INC., Cambridge, MA (US)

(72) Inventors: Christopher Werley, Boston, MA (US); Steven Wasserman, Cambridge, MA (US); Adam Cohen, Cambridge, MA (US)

(73) Assignee: Q-STATE BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 15/574,650

(22) PCT Filed: May 20, 2016

(86) PCT No.: PCT/US2016/033539
§ 371 (c)(1),
(2) Date: Nov. 16, 2017

(87) PCT Pub. No.: WO2016/187543
PCT Pub. Date: Nov. 24, 2016

(65) Prior Publication Data
US 2018/0136446 A1    May 17, 2018

Related U.S. Application Data

(60) Provisional application No. 62/164,905, filed on May 21, 2015.

(51) Int. Cl.
*G01N 21/64* (2006.01)
*G02B 21/16* (2006.01)
(Continued)

(52) U.S. Cl.
CPC ........... *G02B 21/16* (2013.01); *G01N 21/648* (2013.01); *G01N 21/6428* (2013.01);
(Continued)

(58) Field of Classification Search
CPC .. G01N 15/0205; G01N 21/552; G02B 21/16; G02B 21/6458; G02B 21/0088;
(Continued)

(56) References Cited

U.S. PATENT DOCUMENTS 3,975,084 A * 8/1976 Block ................ G01N 15/0205
250/574
5,356,802 A    10/1994 Chandrasegaran
(Continued)

OTHER PUBLICATIONS

S. Simon, "Partial internal reflections on total internal reflection fluorescent microscopy," 2009, Cell Press, pp. 661-668.*
(Continued)

*Primary Examiner* — Kiho Kim
(74) *Attorney, Agent, or Firm* — Brown Rudnick LLP; Thomas C. Meyers

(57) ABSTRACT

The invention provides an open-stage near-TIRF microscope in which all of the optical components are positioned underneath the sample, allowing for physical access to, and control over the environment of, the sample. The microscope can be used to image cells expressing fluorescent voltage indicators. Since the TIRF components do not interfere with the sample, living cells can be studied using a microscope of the invention. Where a sample includes electrically active cells expressing fluorescent voltage indicators, the microscope can be used to view voltage changes in, and thus the electrical activity of, those cells.

20 Claims, 24 Drawing Sheets

(51) Int. Cl.
*G02B 21/06* (2006.01)
*G02B 21/08* (2006.01)
*G02B 21/00* (2006.01)
*G02B 21/10* (2006.01)

(52) U.S. Cl.
CPC ..... *G01N 21/6458* (2013.01); *G02B 21/0088* (2013.01); *G02B 21/06* (2013.01); *G02B 21/086* (2013.01); *G02B 21/10* (2013.01)

(58) Field of Classification Search
CPC ...... G02B 21/10; G02B 21/088; G02B 21/06; G02B 21/648
See application file for complete search history.

(56) References Cited

U.S. PATENT DOCUMENTS

| | | |
|---|---|---|
| 5,436,150 A | 7/1995 | Chandrasegaran |
| 5,487,994 A | 1/1996 | Chandrasegaran |
| 5,591,444 A | 1/1997 | Boss, Jr. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,243,197 B1 | 6/2001 | Schalz |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,885,492 B2 | 4/2005 | DeSimone et al. |
| 6,898,004 B2 | 5/2005 | Shimizu et al. |
| 6,903,185 B2 | 6/2005 | Kim et al. |
| 6,972,892 B2 | 12/2005 | DeSimone et al. |
| 7,153,949 B2 | 12/2006 | Kim et al. |
| 7,459,333 B2 | 12/2008 | Richards et al. |
| 7,560,709 B2 | 7/2009 | Kimura et al. |
| 7,824,869 B2 | 11/2010 | Hegemann et al. |
| 7,964,853 B2 | 6/2011 | Araya |
| 8,202,699 B2 | 6/2012 | Hegemann et al. |
| 8,403,160 B2 | 3/2013 | Hentzel |
| 8,532,398 B2 | 9/2013 | Filkins et al. |
| 8,562,658 B2 | 10/2013 | Shoham et al. |
| 8,580,937 B2 | 11/2013 | Spudich et al. |
| 8,603,790 B2 | 12/2013 | Deisseroth et al. |
| 8,603,809 B2 | 12/2013 | Kruse |
| 8,617,876 B2 | 12/2013 | Farrar et al. |
| 8,629,256 B2 | 1/2014 | Looger et al. |
| 8,647,870 B2 | 2/2014 | Hegemann et al. |
| 8,716,447 B2 | 5/2014 | Deisseroth et al. |
| 9,057,734 B2 | 6/2015 | Cohen et al. |
| 9,207,237 B2 | 12/2015 | Cohen et al. |
| 9,594,075 B2 | 3/2017 | Eggan et al. |
| 2003/0179374 A1 | 9/2003 | Jaaskelainen |
| 2005/0064474 A1 | 3/2005 | Urnov et al. |
| 2005/0202398 A1 | 9/2005 | Hegemann et al. |
| 2006/0188987 A1 | 8/2006 | Guschin et al. |
| 2007/0087959 A1 | 4/2007 | Sfeir et al. |
| 2008/0131962 A1 | 6/2008 | Miller |
| 2009/0118333 A1 | 5/2009 | Chen et al. |
| 2009/0215106 A1 | 8/2009 | Pribilla et al. |
| 2011/0023144 A1 | 1/2011 | Weinstein et al. |
| 2012/0214236 A1 | 8/2012 | Bhatia et al. |
| 2012/0264623 A2 | 10/2012 | Fortunel et al. |
| 2013/0050813 A1 | 2/2013 | Kim et al. |
| 2013/0068967 A1 | 3/2013 | Kleppe et al. |
| 2013/0224756 A1 | 8/2013 | Cohen et al. |
| 2013/0274838 A1 | 10/2013 | Entcheva et al. |
| 2014/0104680 A1 | 4/2014 | Berman et al. |
| 2014/0135382 A1 | 5/2014 | Spudich et al. |
| 2014/0295413 A1 | 10/2014 | Cohen et al. |
| 2014/0326922 A1 | 11/2014 | Zhuang et al. |
| 2015/0301028 A1 | 10/2015 | Eggan et al. |
| 2015/0301029 A1 | 10/2015 | Eggan et al. |
| 2016/0069876 A1 | 3/2016 | Cohen et al. |

OTHER PUBLICATIONS

Flytzanis, 2014, Archaerohodopsin variants with enhanced voltage-sensitive fluorescence in mammalian and Caenorhabditis elegans neurons, Nat Comm 5:4894.
Fong, 2013, Genetic correction of tauopathy phenotypes in neurons derived from human induced pluripotent stem cells, Stem Cell Reports 1(3):1-9.
Foust, 2010, Action potentials initiate in the axon initial segment and propagate through axon collaterals reliably in cerebellar Purkinje neurons, J. Neurosci 30:6891-6902.
Gong, 2013, Enhanced Archaerohodopsin fluorescent protein voltage indicators, PLoSOne 8(6):e66959.
Gong, 2014, Imaging neural spiking in brain tissue using FRET-opsin protein voltage sensors, Nat Comm 5:3674.
Gordon, 2013, Amyotrophic later sclerosis: an update for 2013 clinical features, pathophysiology, management, and therapeutic trials, Aging and Disease 4(5):295-310.
Govorunova, 2013, Characterization of a highly efficient blue-shifted channelrhodopsin from the marine alga *Platymonas subcordiformis*, J Biol Chem 288(41):29911-29922.
Graf, 2011, Historical origins of transdifferentiation and reprogramming, Cell Stem Cell 9:504-516.
Han, 2011, Constructing and deconstructing stem cell models of neurological disease, Neuron 70(4):626-44.
HD iPSC Consortium, 2012, Induced pluripotent stem cells from patients with Huntington's disease show CAG-repeat-expansion-associated phenotypes. Cell Stem Cell 11(2):264-278.
Hick, 2013, Neurons and cardiomyocytes derived from induced pluripotent stem cells as a model for mitochondrial defects in Friedreich's ataxia, Dis Model Mech 6(3):608-21.
Higurashi, 2013, A human Dravet syndrome model from patient induced pluripotent stem cells, Mol Brain 6(1):19.
Hochbaum, 2012, Optopatch-all-optical electrophysiology Abstract, Neuroscience Poster # 229.02 Abstract.
Hochbaum, 2014, All-optical electrophysiology in mammalian neurons using engineered microbial rhodopsins, Nat Meth 11(8):825-833.
Hochbaum, 2014, Bringing bioelectricity to light: all-optical electrophysiology using microbial rhodopsins, PhD Thesis, Harvard University (196 pages).
Hou, 2014, Simultaneous mapping of membrane voltage and calcium in zebrafish heart in vivo reveals chamber-specific developmental transitions in ionic currents, Front Phys 5:344.
Hwang, 2013, Efficient genome editing in zebrafish using a CRISPR-Cas system, Nat. Biotechnol 31:227-229.
Inoue, 2015, Rational design of a high-affinity, fast, red calcium indicator R-CaMP2, Nat Meth 12(1):64-70.
International Search Report and Written Opinion dated Jan. 11, 2016, for International application No. PCT/US15/36181, with International filing date Jun. 17, 2015 (14 pages).
International Search Report and Written Opinion dated Jan. 15, 2016, for PCT/US2015/053721, filed Oct. 2, 2015 (14 pages).
International Search Report and Written Opinion dated Jan. 22, 2016, for PCT/US2015/053711, filed Oct. 2, 2015 (12 pages).
International Search Report and Written Opinion dated Jul. 20, 2015, for International application No. PCT/US2015/026881, with International filing date Apr. 21, 2015 (12 pages).
International Search Report and Written Opinion dated Jul. 20, 2015, for International application No. PCT/US2015/026889 with International filing date Apr. 21, 2015 (13 pages).
International Search Report and Written Opinion dated Jul. 3, 2015, for International Patent Application No. PCT/US2015/026863 with International Filing Date Apr. 21, 2015 (10 pages).
International Search Report and Written Opinion dated Sep. 28, 2015, for International Patent Application No. PCT/US2015/026858 with International Filing Date Apr. 21, 2015 (20 pages).

(56) References Cited

OTHER PUBLICATIONS

International Search Report and Written Opionion dated Sep. 6, 2016, for International Appl. No. PCT/US2016/033539, filed May 20, 2016 (16 pages).
Isalan, 2001, A rapid generally applicable method to engineer zinc fingers illustrated by targeting the HIV-1 promoter, Nat. Biotechnol 19:656-660.
Israel, 2012, Probing sporadic and familial Alzheimer's disease using induced pluripotent stem cells, Nature 482(7384):216-20.
Jackson, 2001, Analysis of lung tumor initiation and progression using conditional expression of oncogenic K-ras, Genes & Dev 15:3243-3248.
Jiao, 2013, Modeling Dravet syndrome using induced pluripotent stem cells (iPSCs) and directly converted neurons, Human Mol Genet 22:4241-4252.
Joung, 2013, TALENs: a widely applicable technology for targeted genome editing, Nat Rev Mol Cell Bio 14:49-55.
Kim,, 2010, Zebrafish model of tuberous sclerosis complex reveals cell-autonomous and non-cell-autonomous functions of mutant tuberin, Dis Model Mech., 4(2):255-67.
Kiskinis, 2014, Pathways disrupted in human ALS motor neurons identified through genetic correction of mutant SOD1, cell Stem Cell (epub).
Klapoetke, 2014, Independent optical excitation of distinct neural populations, Nat Meth 11:338-346.
Koch, 2011, Excitation-induced ataxin-3 aggregation in neurons from patients with Machado-Joseph disease, Nature 480(7378):543-546.
Kondo, 2013, Modeling Alzheimer's disease with iPSCs reveals stress phenotypes associated with intracellular Abeta and differential drug responsiveness, Cell Stem Cell 12(4):487-496.
Kormann, 2011, Expression of therapeutic proteins after delivery of chemically modified mRNA in mice, Nat Biotech 29(2):154-7.
Kralj, 2011, Optical recording of action potentials in mammalian neurons using microbial rhodopsins, Nat Meth 9(1):90-95.
Krey, 2013, Timothy syndrome is associated with activity-dependent dendritic retraction in rodent and human neurons, Nat Neurosci 16(2):201-9.
Ku, 2010, Friedreich's ataxia induced pluripotent stem cells model intergenerational GAA•TTC triplet repeat instability, Cell Stem Cell 7(5):631-7.
Kuo, 2003, Differentiation of monkey embryonic stem cells into neural lineages, Biology of Reproduction 68:1727-1735.
Lee 2009, Modelling pathogenesis and treatment of familial dysautonomia using patient-specific iPSCs, Nature 461:402-406.
Lin, 2009, Characterization of engineered channelrhodopsin variants with improved properties and kinetics, Biophys J 96:1803-1814.
Liu, 2012, Signaling defects in iPSC-derived fragile X premutation neurons, Hum Mol Genet 21:3795-3805.
Liu, 2014, The more the better: modelling Dravet syndrom with induced pluripotent stem cell-derived neurons, Epil curr 14(1):33-34.
Lombardo, 2007, Gene editing in human stem cells using zinc finger nucleases and integrase-defective lentiviral vector delivery, Nat Biotechnol 25(11):1298-306.
Mahammad, 2013, Giant axonal neuropathy-associated gigaxonin mutations impair intermediate filament protein degredation, J Clin Invest 123(5):1964-75.
Makkerh, 1996, Comparative mutagenesis of nuclear localization signals reveals the importance of neutral and acidic amino acids, Current Biology 6:1025-1027.
Marchetto, 2010, A model for neural development and treatment of Rett syndrome using human induced pluripotent stem cells, Cell 143(4):527-39.
Maruyama, 2011, Detection of cells from calcium imaging data by non-negative matrix factorization, 21 Ann Conf. J Neur Net Soc.
Abdelfattah, 2014, Development of a red genetically encoded voltage indicator and its use with channelrhodopsin in all-optical electrophysiology, Biophys J 106(2)Supp 1:629a-630a.

Alami, 2014, Microtubule-dependent transport of TDP-43 mRNA granules in neurons is impaired by ALS-causing mutations, Neuron 81(3):536-543.
Almeida, 2012, Induced pluripotent stem cell models of progranulin-deficient frontotemporal dementia uncover specific reversible neuronal defects, Cell Rep 2(4):789-798.
Almeida, 2013, Modeling key pathological features of frontotemporal dementia with C9ORF72 repeat expansion in iPSC-derived human neurons, Acta Neuropathol 126(3):385-399.
Ambasudhan, 2011, Direct reprogramming of adult human fibroblasts to functional neurons under defined conditions, Cell Stem Cell 9:113-118.
Amoroso, 2013, Accelerated high-yield generation of limb-innervating motor neurons from human stem cells, J Neurosci 33(2):574-86.
An, 2012, Genetic correction of Huntington's disease phenotypes in induced pluripotent stem cells, Cell Stem Cell 11(2):253-263.
Ananiev, 2011, Isogenic pairs of wild type and mutant induced pluripotent stem cell (iPSC) lines from Rett syndrome patients as in vitro disease model, PLoS One 6(9):e25255.
Andrade, 2012, Evidence for premature aging due to oxidative stress in iPSCs from Cockayne syndrome, Hum Mol Genet 21:3825-3834.
Arrenberg, 2010, Optogenetic control of cardiac function, Science 330(6006):971-974.
Ataka, 2002, A genetically targetable fluorescent probe of channel gating with rapid kinetics, Biophys J 82:509-516.
Atasoy, 2009, A FLEX switch targets channelrhodopsin-2 to multiple cell types for imaging and long-range circuit mapping, J Neurosci 28(28):7025-7030.
Badger, 2014, Parkinson's disese in a dish—using stem cells as a molecular tool, Neuropharmacol 76:88-96.
Beerli, 2002, Engineering polydactyl zinc-finger transcription factors, Nat. Biotechnol, 20:135-141.
Beja et al., 2001, Proteorhodopsin phototrophy in the ocean, Nature 411:786-789.
Belfort, 1997, Homing endonucleases: keeping the house in order, Nucleic Acids Res 25(17):3379-3388.
Bilican et al, 2012, Mutant induced pluripotent stem cell lines recapitulate aspects of TDP-43 proteinopathies and reveal cell-specific vulnerability, PNAS 109(15):5803-5808.
Blokhuis, 2013, Protein aggregation in amyotrophic lateral sclerosis, Acta Neuropathol 125:777-794.
Boulting, 2011, A functionally characterized test set of human induced pluripotent stem cells, Nat Biotech 29(3):279-286.
Bozdagi, 2010, Haploinsufficiency of the autism-associated Shank3 gene leads to deficits in synaptic function, social interaction, and social communication, Mol Autism 1 (1): 15.
Brennand, 2011, Modelling schizophrenia using human induced pluripotent stem cells, Nature 473(7346):221-225.
Bruegmann, 2010, Optogenetic control of heart muscle in vitro and in vivo, Nat Meth 7(11):897-900.
Cardin, 2010, Targeted optogenetic stimulation and recording of neurons in vivo using cell-type-specific expression of Channelrhodopsin-2, Nat Protoc 5(2):247-54.
Carlson, 2013, Circular permutated red fluorescent proteins and calcium ion indicators based on mCherry, Protein Eng Des Sel 26(12):763-772.
Caspi, 2009, In vitro electrophysiological drug testing using human embryonic stem cell derived cardiomyocytes, Stem Cells Devel 18(1):161-172.
Chanda, 2005, A hybrid approach to measuring electrical activity in genetically specified neurons, Nat Neuroscience 8:1619-1626.
Chang, 2013, Genome editing with RNA-guided Cas9 nuclease in zebrafish embryos, Cell Res 23:465-472.
Chaudhary, 2014, Measurement of optical action potentials and calcium transients in hIPSC-derived cardiomyocytes using the novel Optopatch fluorescent platform, poster presented in Oct. 2014.
Chen, 2013, Ultra-sensitive fluorescent proteins for imaging neuronal activity, Nature 499(7458):295-300.

(56) References Cited

OTHER PUBLICATIONS

Chiang, 2011, Integration-free induced pluripotent stem cells derived from schizophrenia patients with a DISC1 mutation, Molecular Psych 16:358-360.
Chow, 2010, High-performance genetically targetable optical neural silencing by light-driven proton pumps, Nature 463:98-102.
Chung, 2013, Identification and rescue of a-synuclein toxicity in Parkinson patient-derived neurons, Science 342(6161):983-7.
Cohen, 2013, All-optical electrophysiology with microbial rhodopsins, Event Page for lecture on Feb. 4, 2013, retrieved from the internet on Oct. 29, 2015, at: <<http://www.fitzpatrick.duke.edu/events/all-optical-electrophysiology-microbial-rhodopsins-0>>.
Cooper, 2012, Pharmacological rescue of mitochondrial deficits in iPSC-derived neural cells from patients with familial Parkinson's disease, Sci Transl Med 4(141):141ra90.
Corti, 2012, Genetic correction of human induced pluripotent stem cells from patients with spinal muscular atrophy, Sci Transl Med 4 (165):165ra162.
Dan, 2013, DMD-based LED-illumination super-resolution and optical sectioning microscopy, Sci Rep 3:1116.
Dana, 2016, Sensitive red protein calcium indicators for imaging neural activity, bioRxiv, first published online Feb. 29, 2016, and available at biorxiv.org/content/biorxiv/early/2016/02/29/041780.full.pdf.
Davis, 2012, Cardiomyocytes derived from pluripotent stem cells recapitulate electrophyisiological characteristics of an overlap syndrome of cardiac sodium channel disease, Circulation 125(25):3079-3091.
Davis-Dusenbery, 2014, How to make spinal motor neurons, Development 141(3):491-501.
Denton, 2014, Loss of spastin function results in disease-specific axonal defects in human pluripotent stem cell-based models of hereditary spastic paraplegia, Stem Cells 32(2):414-23.
Diester, 2011, An optogenetic toolbox designed for primates, Nat Neurosci 14(3):387-97.
Dilas, 2012, 638nm, conduction-Cooled Single Bars product guide, DILAS Diode Laser, Inc., Tucson AZ (2 pages).
Dimos, 2008, Induced pluripotent stem cells generated from patients with ALS can be differentiated into motor neurons, Science 321(5893):1218-21.
Donnelly, 2013, RNA toxicity from the ALS/FTD C9orf72 expansion is mitigated by antisense intervention, Neuron 80(2):415-28.
Dottori, 2011, Neural development in human embryonic stem cells-applications of lentiviral vectors, J Cell Bio 112(8):1955-62.
Du, 2012, Role of mismatch repair enzymes in GAA.TTC triplet-repeat expansion in Friedreich ataxia induced pluripotent stem cells, J Biol Chem 287(35):29861-29872.
Ebert, 2009, Induced pluripotent stem cells from a spinal muscular atrophy patient, Nature 457(7227):277-80.
Egawa, 2012, Drug screening for ALS using patient-specific induced pluripotent stem cells, Sci Transl Med 4(145):145ra104.
EPI4K Consortium, 2013, De novo mutations in epileptic encephalopathies, Nature 501:217-221.
Exam report dated Dec. 5, 2017, for EP Application No. 15 720 856.2 (15 pages).
Vierbuchen, 2010, Direct conversion of fibroblasts to functional neurons by defined factors, Nature4 63:1035-1041.
Wah, 1998, Structure of FokI has implications for DNA cleavage, PNAS 95:10564-10569.
Wainger, 2014, Intrinsic membrane hyperexcitability of amyotrophic lateral sclerosis patient-derived motor neurons, Cell Reports 7(1):1-11.
wang, 2011, Synaptic dysfunction and abnormal behaviors in mice lacking major isoforms of Shank3, Hum. Mol. Genet. 20 (15): 3093-108.
Wardill, 2013, A neuron-based screening platform for optimizing genetically-encoded calcium indicators, PLoS One 8(10):e77728.
Wernig, 2002, Tau EGFP embryonic stem cells: an efficient tool for neuronal lineage selection and transplantation. J Neuroscience Res 69:918-24.

Wlodarski,, 2008, Tuberin-heterozygous cell line TSC2ang1 as a model for tuberous sclerosis-associated skin lesions, Int J Mol Med. 21(2):245-50.
Wu, 2013, Improved orange and red Ca2+ indicators and photophysical considerations for optogenetic applications, ACS Chem Neurosci 4(6):963-972.
Xiao, 2013, Chromosomal deletions and inversions mediated by TALENS and CRISPR/Cas in zebrafish, Nucl Acids Res 1-11.
Yang, 2013, A small molecule screen in stem-cell-derived motor neurons identifies a kinase inhibitor as a candidate therapeutic for ALS, Cell Stem Cell 12(6):713-726.
Yizhar, 2011, Optogenetics in neural systems, Neuron 71(1):9-34.
Yoo, 2011, MicroRNA mediated conversion of human fibroblasts to neurons, Nature 476:228-231.
Zangi, 2013, Modified mRNA directs the fate of heart progenitor cells and induces vascular regeneration after myocardial infarction, Nat Biotech 31:898-907.
Zhang, 2013, Rapid single-step induction of functional neurons from human pluripotent stem cells, Neuron 78(5):785-798.
Zhao, 2011, An expanded palette of genetically encoded Ca2+ indicators, Science 333(6051):1888-1891.
Zoghbi, 2012, Synaptic Dysfunction in Neurodevelopmental Disorders Associated with Autism and Intellectual Disabilities, Cold Spring Harb Perspect Biol. 4(3), J Neurol Sci. 217(1):47-54.
Mattis, 2011, Principles for applying optogenetic tools derived from direct comparative analysis of microbial opsins, Nat. Meth. 9:159-172.
Mazzulli, 2011, Gaucher disease glucocerebrosidase and a-synuclein form a bidirectional pathogenic loop in synucleinopathies, Cell 146(1):37-52.
Meikle, 2007, A mouse model of tuberous sclerosis: neuronal loss of Tsc1 causes dysplastic and ectopic neurons, reduced myelination, seizure activity, and limited survival, J Neurosci. 27(21):5546-58.
Meikle, 2008, Response of a neuronal model of tuberous sclerosis to mammalian target of rapamycin (mTOR) inhibitors: effects on mTORC1 and Akt signaling lead to improved survival and function, J Neurosci., 28(21):5422-32.
Melkonian, 1986, A light and electron microscopic study of *Scherffelia dubia*, a new member of the scaly green fagellates (*Prasinophyceae*). Nord. J. Bot. 6:235-256.
Moehle, 2007, Targeted gene addition into a specified location in the human genome using designed zinc finger nucleases PNAS 104:3055-3060.
Molokanova, 2008, Bright future of optical assays for ion channel drug discovery, Drug Discov Today 13:14-22.
Mordwinkin, 2013, A review of human pluripotent stem cell-derived cardiomyocytes for high-throughput drug discover, cardiotoxicity screening and publication standards, J Cardiovasc Trans Res 6(1):22-30.
Mukamel, 2009, Automated analysis of cellular signals from large-scale calcium imaging data, Neuron 63(6):747-760.
Muratore, 2014, The familial Alzheimer's disease APPV717I mutation alters APP processing and tau expression in iPSC-derived neurons, Human Molecular Genetics, in press.
Musaro, 2010, State of the art and the dark side of amyotrophic lateral sclerosis, WJBC 1(5):62-68.
Nagel, 2005, Light activation of channelrhodopsin-2 in excitable cells of Caenorhabditis elegans triggers rapid behavioral responses, Curr. Biol. 15, 2279-2284.
Nakai, 2001, A high signal-to-noise Ca(2+) probe composed of a single fluorescent protein, Nat Biotech 19:137-141.
Neutze, 2002, Bacteriorhodopsin: a high-resolution structural view of vectorial proton transport, Biochimica et Biophysica Acta 1565:144-167.
Nicita, 2012, The genetics of monogenic idiopathic epilepsies and epileptic encephalopathies, Seizure 21:3-11.
Nihei, 2013, Enhanced aggregation of androgen receptor in induced pluripotent stem cell-derived neurons from spinal and bulbar muscular atrophy, J Biol Chem 288(12):8043-52.
Normand, 2013, Temporal and mosaic Tsc1 deletion in the developing thalamus disrupts thalamocortical circuitry, neural function, and behavior, Neuron, 5;78(5):895-909.

(56) References Cited

OTHER PUBLICATIONS

Pang, 2011, Induction of human neuronal cells by defined transcription factors, Nature 476:220-223.
Parent, 2015, Reprogramming patient-derived cells to study the epilepsies, Nat Neurosci 18:360-366.
Pasinelli, 2006, Molecular biology of amyotrophic lateral sclerosis: insights from genetics, Nat Rev Neurosci 7:710-723.
Peça, 2011, Shank3 mutant mice display autistic-like behaviours and striatal dysfunction, Nature 472 (7344): 437-42.
Piao, 2015, Combinatorial mutagenesis of the voltage-sensing domain enables the optical resolution of action potentials tiring at 60 Hz by a genetically encoded fluorescent sensor of membrane potential, J Neurosci 35(1):372-385.
Popovic 2011, The spatio-temporal characteristics of action potential initiation in layer 5 pyramidal neurons: a voltage imaging study, J. Physiol. 589:4167-4187.
Przybylo, 2010, Fluorescence techniques for determination of the membrane potentials in high throughput screening, J Fluoresc 20(6):1139-1157.
Reinhardt, 2013, Genetic correction of a LRRK2 mutation in human iPSCs links parkinsonian neurodegeneration to ERK-dependent changes in gene expression, Cell Stem Cell 12(3):354-367.
Rothermel, 2013, Transgene expression in target-defined neuron populations mediated by retrograde infection ith adeno-associated viral vectors, J Neurosci 33(38):195-206.
Rotunno, 2013, An emerging role for misfolded wild-type SOD1 in sporadic ALS pathogenesis, Front Cell Neurosci 7:a253.
Saccon, 2013, Is SOD1 loss of function involved in amyotrophic lateral sclerosis?, Brain 136:2342-2358.
Sager, 2014, Rechanneling the cardiac proarrythmia safety paradigm: a meeting from the cardiac safety research consortium, Am Heart J 167(3):292-300.
Sanders, 2013, LRRK2 mutations cause mitochondrial DNA damage in iPSC-derived neural cells from Parkinson's disease patients: reversal by gene correction. Neurobiol Dis 62:381-6.
Santiago, 2008, Targeted gene knockout in mammalian cells by using engineered zinc-finger nucleases, PNAS 105:5809-5814.
Sapunar, 2012, Dorsal root ganglion—a potential new therapeutic target for neuropathic pain, J Pain Res 1:31-38.
Sareen, 2012, Inhibition of apoptosis blocks human motor neuron cell death in a stem cell model of spinal muscular atrophy. PLoS One 7(6):e39113.
Sauer, 1988, Site-specific DNA recombination in mammalian cells by the Cre recombinase of bacteriophage P1, PNAS 85:5166-70.
Saunders, 2012, Novel recombinant adeno-associated viruses for Cre activated and inactivated transgene expression in neurons, Front Neural Circuits 6:47.
Seibler, 2011, Mitochondrial Parkin recruitment is impaired in neurons derived from mutant PINK1 induced pluripotent stem cells, J Neurosci 31(16):5970-6.
Shi, 2012, A human stem cell model of early Alzheimer's disease pathology in Down syndrome, Sci Transl Med 4(124):124ra129.
Siegel, 1997, A genetically encoded optical probe of membrane voltage. Neuron 19:735-741.
Sineshchekov, 2004, Light-induced intramolecular charge movements in microbial rhodopsins in intact *E. Coli* cells, Photochem Photobiol Sci 3:548-554.
Son, 2011, Conversion of mouse and human fibroblasts into functional spinal motor neurons, Cell Stem Cell 9:205-218.
Song, 2012, Neural differentiation of patient specific iPS cells as a novel approach to study the pathophysiology of multiple sclerosis, Stem Cell Res 8(2):259-73.
St-Pierre, 2014, High-fidelity optical reporting of neuronal electrical activity with an ultrafast fluorescent voltage sensor, Nat Neurosci 17(6):884.
Subramaniam, 1992, Aspartic acid 85 in bacteriorhodopsin functions both as proton acceptor and negative counterion to the Schiff base, J Biol Chem 267(36):25730-25733.
Sánchez-Danés, 2012, Disease-specific phenotypes in dopamine neurons from human iPS-based models of genetic and sporadic Parkinson's disease, EMBO Mol Med, 4: 380-395.
Takahashi, 2006, Induction of pluripotent stem cells from mouse embryonic and adult fibroblast cultures by defined factors Cell 126:663-676.
Takahashi, 2007, Induction of pluripotent stem cells from adult human fibroblasts by defined factors, Cell 131:861-872.
Thomas, 2014, The hidden genetics of epilepsy—a clinically important new paradigm, Nature Rev 10:283-292.
Trounson, 2012, Human disease modeling with induced pluripotent stem cells, Curr Op Gen Dev 22(5):509-516.
Urnov, 2005, Highly efficient endogenous human gene correction using designed zinc-finger nucleases, Nature 435(7042):646-51.
Vazin, 2014, Efficient derivation of cortical glutamatergic neurons from human pluripotent stem cells: A model system to study neuortoxicity in Alzheimer's disease, Neurobiol Dis 62:62-72.
European search report dated Nov. 28, 2018, for European patent application No. 16797384.1 (18 pages).
Axelrod, 2001, Total internal reflection fluorescence microscopy in cell biology, Traffic 2:764-774.
Sluder, 2013, Fluorescent protein applications in Micrsocopy, Chapter 5 in Digital Microscopy, sluder & Wolf, Eds., Elsevier.
Fest, 2013, Baffle and cold shield design, Chapter 9 in Stray Light Analysis and Control, Society of Photo-Optical Instrumentation Engineers (SPIE) (pp. 163-182).
TIRF Labs, 2016, Prims-based TIRF Microscopy, Brochure (2 pages).

* cited by examiner

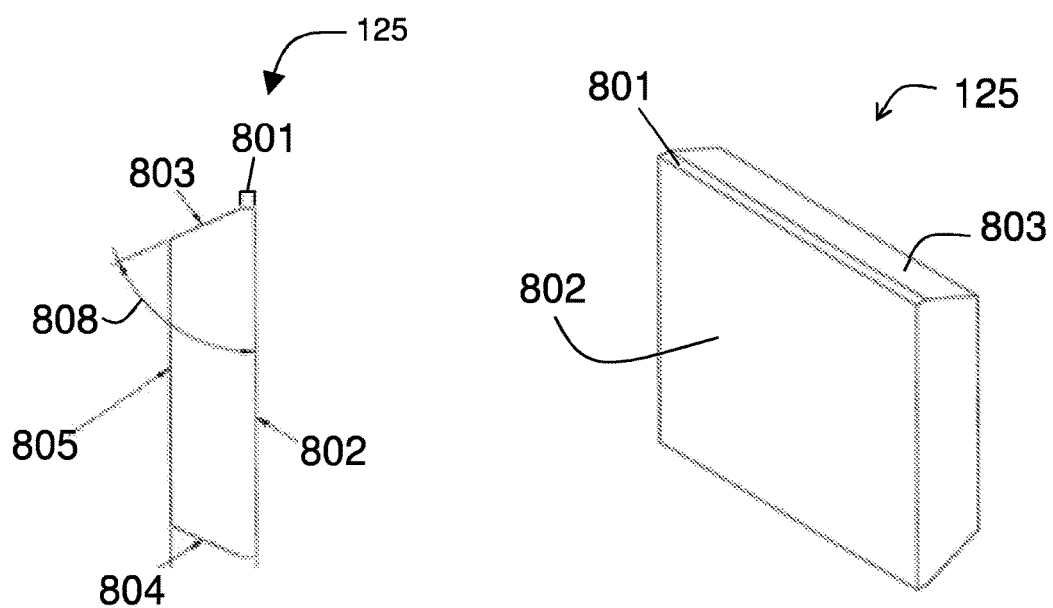
FIG. 13A
FIG. 13B
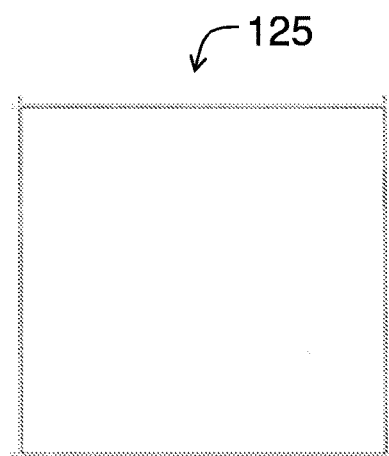
FIG. 13C

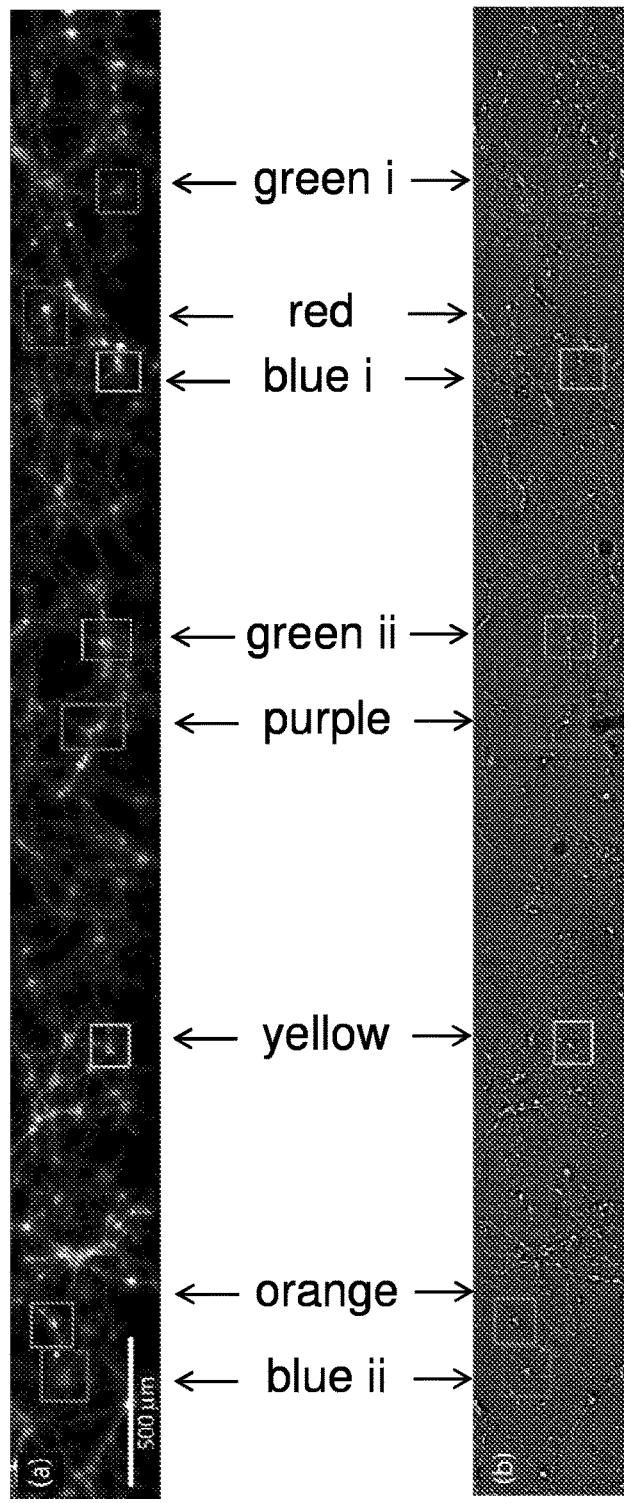
FIG. 17  FIG. 18

OPTOGENETICS MICROSCOPE

CROSS-REFERENCE TO RELATED APPLICATION

This application claims priority and benefit of U.S. Provisional Patent Application No. 62/164,905, filed May 21, 2015, the contents of which are incorporated by reference.

FIELD OF THE INVENTION

The invention generally relates to microscopy, and specifically to near total internal reflection microscopy.

BACKGROUND

Heart disease and Alzheimer's are examples of diseases that involve electrically active cells, such as neurons and cardiomyocytes. Studying those cells is therefore important to helping people faced with such diseases.

One method of studying biological samples is fluorescence microscopy, a technique in which fluorophores are bound to the specimen to detect phenomena such as cell surface binding, neurotransmitter release, or specific DNA sequences. However, fluorophores and other compounds in the surrounding medium and even in the optical components of the microscope can autofluoresce and overwhelm fluorescence from the sample. Attempts have been made to reduce background fluorescence by using total internal reflection fluorescence (TIRF) microscopy. A TIRF microscope illuminates only a thin region of the sample so that fluorophores in the surrounding medium do not receive the excitation energy needed for fluorescence. However, existing TIRF microscopes require a prism to be pressed down onto the sample in a configuration that severely limits what conditions are allowable for the sample. For example, the TIRF prism occludes any culture media, as would be required for living cells, and prevents any physical access to the sample. Thus, fluorescence microscopy has not proven satisfactory for studying fine details of living, electrically active cells.

SUMMARY

The invention provides a near-TIRF microscope in which all of the optical components are positioned underneath the sample and illumination occurs from the side rather than through the objective lens. The side illumination allows the microscope to have more intense illumination and a larger field of view. The microscope can be referred to as an "open-stage" microscope, because the area above the stage is unencumbered by optical elements such as prisms. That configuration allows for physical access to the sample and control over its environment. Thus the sample can be, for example, living cells in a nutrient medium. That configuration solves many of the problems associated with traditional TIRF microscopes. In particular, a thin region of sample cells can be illuminated with a TIRF or near-TIRF beam without having to physically interfere with the cells by loading them into a flow chamber. Instead, living cells in an aqueous medium such as a maintenance broth can be observed. The sample can be further analyzed from above with electrodes or other equipment as desired. Due to that advantageous configuration, an open-stage TIRF microscope can be used to image cells expressing fluorescent voltage indicators. Since the TIRF components do not interfere with the sample, living cells can be studied using a microscope of the invention. Where a sample includes electrically active cells expressing fluorescent voltage indicators, the microscope can be used to view voltage changes in, and thus the electrical activity of, those cells. Since the electrical activity of cells such as neurons and cardiomyocytes can be studied using devices and methods of the invention, the invention will help researchers understand diseases affecting those cells, empowering them to discover new preventions and cures for diseases such as Alzheimer's and heart disease.

Devices and methods of the present invention can be used in conjunction with optogenetics. In optogenetics, light is used to control and observe certain events within living cells. For example, a light-responsive gene such as a fluorescent voltage indicator can be introduced into a cardiomyocyte. The reporter may be a rhodopsin-type transmembrane protein that generates an optical signal in response to changes in membrane potential, thereby functioning as an optical reporter. For example modified versions of the microbial rhodopsin protein Archaerhodopsin 3 (Arch) from *Halorubum sodomense* may be used as an optically reporter. Examples of optical reporters are the microbial rhodopsin QuasAr2 and QuasAr3. When excited with an illumination light at one wavelength, the reporter is energized to emit a light of a different wavelength indicative of a change in membrane potential. The microscope therefore includes an illumination system for illuminating the sample with one wavelength of light and an imaging system for recording an image of light given off by the reporter in a different wavelength. The illumination system includes a light source and a prism. Illumination light from the light source is transmitted through the prism, which imparts near-TIRF illumination on the sample. The imaging system includes an objective lens and an image sensor for recording the light emitted by the reporter.

Near-TIRF illumination can provide illumination of a thin region of cells approximately 10 microns thick. That means that it can illuminate a whole cell that is in contact with a sample dish. TIRF, on the other hand, creates an evanescent wave along the surface of the interface of reflection, thereby illuminating only a few hundred nanometers, or merely a small portion of the cell. The near-TIRF illumination comes from the side rather than through the objective, and so the near-TIRF microscope is able to illuminate a whole cell using intense illumination without illuminating the medium or other optical components.

Optionally, cells in the sample may also include optogenetic activators, such as a light-gated ion channel. The optical actuator may be a genetically-encoded rhodopsin or modified rhodopsin such as a microbial channel rhodopsin. For example, sdChR, a channel rhodopsin from *Scherffelia dubia*, may be used or an improved version of sdChR—dubbed CheRiff—may be used as an optical actuator. "CheRiff" refers to a version of sdChR that uses mouse codon optimization, a trafficking sequence, and the mutation E154A as described herein. The activator responds to light of a particular wavelength to initiate an action potential in the electrically active cell. To activate those optogenetic proteins, the microscope may include an activation system. The activation system directs light onto the sample at a wavelength capable of activating the channel rhodopsin. The activation light may be patterned light, which corresponds to certain areas of the sample, such as particular cells in the sample. The pattern can be imparted on the light beam with a spatial light modulator (SLM) such as a digital micromirror device (DMD). Light is shined onto the SLM, which reflects a defined pattern of the light onto the sample. The light pattern can correspond to particular cells expressing the activator.

The microscope may include additional reporters and associated systems for activating them. Proteins that report changes in intracellular calcium levels may be used, such as a genetically-encoded calcium indicator (GECI). The microscope may include a subsystem to provide activation light for a GECI, such as yellow light for RCaMP. Exemplary GECIs include GCaMP or RCaMP variants such as for example, jRCaMP1a, jRGECO1a, or RCaMP2. A key challenge in combining multiple optical modalities (e.g. optical excitation, activation, voltage imaging, calcium imaging) is to avoid optical crosstalk between the modalities. The pulses of light used to deliver optical activation should not induce fluorescence of the reporters; the light used to image the reporters should not activate the light-gated ion channel; and the fluorescence of one reporter should be readily distinguished from the fluorescence of other reporters. In some aspects of the invention, this separation of modalities is achieved by selecting an activator and reporters with little or no spectral overlap. In one embodiment, the activator is activated by blue light, a Ca2+ reporter is excited by yellow light and emits orange light, and a voltage reporter is excited by red light and emits near infrared light.

In certain aspects, the invention provides a near-TIRF microscope. The microscope includes a stage having an object region configured to support a sample and an illumination subsystem with a prism disposed beneath the object region and a light source operable to transmit light onto the prism to cause the prism to illuminate the sample from beneath by near total internal reflection. The microscope includes an imaging subsystem with an objective lens unit disposed beneath the prism and an image capture device operable to receive an image of the sample that is passed through the objective lens unit from the object region.

In some embodiments, the object region may support the sample by means of a sample dish with a transparent bottom portion. The transparent bottom portion of the sample dish can be provided by a coverslip mounted to a surrounding dish structure. The prism and transparent bottom portion may be coupled by a low-autofluorescence index matching fluid; and the prism, the index matching fluid, and the transparent bottom portion may have a common index of refraction. The object region may comprise a dish with cells in an aqueous medium. The sample dish can be configured to hold an aqueous medium and provide access to the sample from above.

In certain embodiments, the microscope may include an environmental control subsystem operable to control environmental conditions above the aqueous medium to maintain living cells in the aqueous medium. The environmental control subsystem can control humidity, temperature, and other factors of the sample region.

In some embodiments, the illumination light source is a diode laser bar, a diode laser, another type of laser, or an LED. The illumination light may have a wavelength capable of exciting a microbial rhodopsin, such as QuasAr2 or QuasAr3. The wavelength of the illumination light may be, for example, between 580 and 650 nm. The illumination light may have an intensity between 10 and 400 W/cm2 and preferably about 100 W/cm2. The illumination subsystem may include baffles positioned to prevent unwanted reflected or refracted illumination light from entering the objecting lens. The illumination subsystem may also have other beam shaping optics disposed within a path defined by the illumination light.

In certain embodiments, the objective lens has a numerical aperture between 0.4 and 1.0, inclusive, and preferably about 0.5. The image capture device may be a camera, such as a CMOS camera. The camera may have a field of view sufficient to capture at least one cell, and up to dozens or hundreds or thousands of cells, such as about five hundred cells. The image capture device may have a minimum exposure time 1 ms or less, and may acquire images at 500 to 2000 Hz or preferably about 1 kHz.

In embodiments, the microscope includes an activation subsystem comprising an activation light source configured to transmit activation light that is spectrally distinct from the illumination light onto the sample. The activation light source can be a diode laser bar, a diode laser, an LED, or any other suitable light source. The activation subsystem may transmit the activation light upwards through the objective lens unit and onto the sample. The activation subsystem can include an activation tube lens disposed within a path defined by the activation light, operable to focus the activation light at a back aperture of the objective lens. It may also include a dichroic mirror to reflect the activation light upwards onto the sample. The dichroic mirror is further configured to allow the imaging light to pass downward through it to the image capture device. In embodiments, the activation light has a wavelength capable of exciting a light-sensitive activator protein. The light-sensitive activator protein may be a light-gated ion channel, such as CheRiff. The wavelength of the activation light can be, for example, between 450 and 495 nm. The activation light may have an intensity of about 22 mW/cm2.

The activation subsystem may be further operable to spatially pattern the activation light onto the sample, such as with a spatial light modulator (SLM). The spatial light modulator may be a digital micromirror device, a digital light processor (DLP), a liquid crystal display, or another suitable SLM. The SLM can be controlled by a computer. The computer may define an illumination pattern. The illumination pattern can be input by a user or it can be generated by the computer based on an input from the imaging subsystem, such as a pattern of one or more cells in the sample. The computer may define an illumination pattern with the spatial light modulator that corresponds to the pattern of cells in the sample, thereby causing the activation subsystem to transmit illumination light onto the one or more cells.

In embodiments, the microscope may be configured to transmit a second illumination light. The second illumination light may have a wavelength capable of exciting a light-sensitive reporter protein such as a light-sensitive calcium-indicating protein.

In certain aspects, the invention provides a method for imaging a sample. The method includes positioning a sample dish in an object region of a stage of a fluorescence microscopy instrument, wherein the sample dish comprises a transparent bottom portion and contains a biological sample in an aqueous medium. The method further includes illuminating the biological sample from beneath via an illumination light passing through a prism disposed underneath the transparent bottom portion, whereby the prism imparts near total internal reflection on the illumination light. The method further includes imaging the biological sample through the transparent bottom portion using an imaging subsystem of the instrument, the imaging subsystem comprising an objective lens unit disposed beneath the sample dish and an image capture device.

In some embodiments, the transparent bottom portion of the sample dish can be provided by a coverslip mounted to a surrounding dish structure. The prism and transparent bottom portion may be coupled by a low-autofluorescence index matching fluid; and the prism, the index matching fluid, and the transparent bottom portion may have a common index of reflection. The sample dish can be configured to hold an aqueous medium and provide access to the sample from above.

In certain embodiments, the method may include using an environmental control subsystem to control environmental conditions above the aqueous medium to maintain living cells in the aqueous medium. The environmental control subsystem can control humidity, temperature, gas, and other factors of the sample region.

In some embodiments of the method, the illumination light source is a diode laser bar, a diode laser, other form of laser, or an LED. The illumination light may have a wavelength capable of exciting a microbial rhodopsin, such as QuasAr2 or QuasAr3. The wavelength of the illumination light may be, for example, between 580 and 650 nm. The illumination light may have an intensity between 10 to 400 W/cm2 and preferably about 100 W/cm2. The method may further comprise a second illumination light capable of exciting RCaMP. The wavelength of illumination light may be, for example, between 530 and 580 nm. The second illumination light may have an intensity of about 1 W/cm2.

The method may further comprise using baffles positioned to block unwanted reflected light from entering the objecting lens. The method may further comprise shaping the illumination light beam using beam-shaping optics disposed within a path defined by the illumination light.

In certain embodiments, the objective lens has a numerical aperture between 0.4 and 1.0, inclusive, and preferably about 0.5. The image capture device may be a camera, such as a CMOS camera. The camera may have a field of view sufficient to capture at least one cell, and up to dozens or hundreds of cells, and up to about five hundred cells. The image capture device may have a minimum exposure time 2 ms or less, and preferably is 1 ms or less and may acquire images at 1 kHz.

In embodiments, the method includes transmitting an activation light onto the sample using an activation subsystem comprising an activation light source. The activation light is spectrally distinct from the illumination light. The activation light source can be a diode laser bar, a diode laser, or other type of laser, an LED, or any other suitable light. The activation subsystem may transmit the activation light upwards through the objective lens unit and onto the sample. The method can include focusing the activation light at a back aperture of the objective lens using an activation tube lens disposed within a path defined by the activation light. It may also include reflecting the activation light upwards onto the sample using a dichroic mirror, and allowing the imaging light to pass downward through the dichroic mirror to the image capture device. In embodiments, the activation light has a wavelength capable of activating a light-sensitive activator protein. The light-sensitive activator or protein may be a light-gated ion channel, such as CheRiff. The wavelength of the activation light can be, for example, between 450 and 495 nm. The activation light may have an intensity between 10 to 200 mW/cm2 and preferably about 22 mW/cm2.

In some embodiments, the method includes spatially patterning the activation light using a spatial light modulator (SLM). The spatial light modulator may be a digital micromirror device, a digital light processor (DLP), a liquid crystal display, or another suitable SLM. The SLM can be controlled by a computer. The method may involve controlling the SLM with a computer. It may further involve defining an illumination pattern using the computer. In embodiments, the illumination pattern can be input by a user or it can be generated by the computer based on an input from the imaging subsystem, such as a pattern of one or more cells in the sample. The method may involve defining with the computer an illumination pattern with the spatial light modulator that corresponds to the pattern of cells in the sample, thereby causing the activation subsystem to transmit illumination light onto the one or more cells.

In embodiments, the method may include transmitting a second illumination light onto the sample. The second illumination light may have a wavelength capable of exciting a light-sensitive reporter protein such as a light-sensitive calcium-indicating protein.

A microscope of the invention preferably includes a high-resolution, large FOV imaging system. The imaging system may include an objective lens, a tube lens, optical filters, mirrors, a focusing mechanism, and other optical elements to form an image in an image plane. The imaging system may also include an image detector that resides in the image plane of the imaging system for recording fluorescence images of the sample.

The illumination subsystem provides light to excite fluorescent indicators in the sample. The illumination subsystem includes a light source of appropriate wavelength and power. Light sources may include diode lasers, diode bar lasers, other types of lasers, LEDs, or other sources with suitable characteristics. Optical filters, mirrors, lenses, prisms, fibers, and other optical elements may be used to alter the spectrum and spatial characteristics of the light source. The illumination subsystem provides near-TIRF illumination through the use of a prism disposed just beneath the sample. The prism preferably includes a low autofluorescence material such as fused silica. Any gap between the prism and the transparent substrate supporting the sample may be filled with an index matching fluid such as microscope immersion oil (such as type FF microscope oil manufactured by Cargille Corporation) with low auto-fluorescence. Since the illumination light for near-TIRF illumination can enter the prism from the side, the illumination light need not pass through the objective lens, which minimizes autofluorescence from glass elements of the objective. The illumination may be coupled into the sample at an angle that is near the total internal reflection angle in order to minimize background fluorescence from the cell growth medium. The near-TIR angle is exhibited at the interface between the sample support (typically a transparent substrate) and the sample itself (which may include for example, living cells in a nutrient media). Illumination may be directed at the sample from multiple directions to further reduce background fluorescence.

The microscope may include an optional activation subsystem for exciting light-sensitive compounds in the sample. The activation subsystem may include one or more light sources and a means for coupling the illumination to the sample. In certain embodiments, the activation subsystem may include a spatial light modulator (SLM) to facilitate selective optical activation of the sample. Light sources may include LEDs, diode lasers, other types of lasers, arc lamps, or other sources with suitable characteristics. Optical filters, mirrors, lenses, prisms, fibers, and other optical elements may be used to alter the spectrum and spatial characteristics of the light source. The SLM may be a digital micromirror device (DMD), liquid crystal display (LCD), or other type of SLM. The SLM may be connected to a computer that controls the light pattern, which may be user-defined or it may be automatically generated by a computer program to correspond to certain features of the sample, such as an individual cell, a group of cells, or a part of a cell. The activation light may be coupled to the sample by a dichroic mirror in the imaging path, a small mirror placed at the back focus of the objective lens, or from above.

Methods of the invention comprise positioning a biological sample in an aqueous medium on the object region of a microscope, illuminating the sample with an illumination light via a prism that imparts near total internal reflection on the illumination light, and imaging the sample with an image capture device through an objective lens disposed beneath the sample. In certain embodiments, the method further comprises using an environmental control subsystem to control environmental conditions such as humidity, temperature, and gas above the aqueous medium to maintain living cells in the sample. The method may further comprise transmitting an activation light onto the sample using an activation subsystem. Activation light can be spatially patterned using a spatial light modulator. The pattern may be defined by a user or by a computer, and may correspond to one or more cells in the sample, such that only certain cells in the sample are activated. The method may further involve the use of optical filters, mirrors, lenses, prisms, fibers, and other optical elements to alter the spectrum and spatial characteristics of the light source.

BRIEF DESCRIPTION OF THE DRAWINGS

FIGS. 13A-13C show various views of a prism for use with the present disclosure.

FIG. 17 is an image of QuasAr in rat hippocampal neurons.

FIG. 18 is a white light image of rat hippocampal neurons.

DETAILED DESCRIPTION

Figure 1:
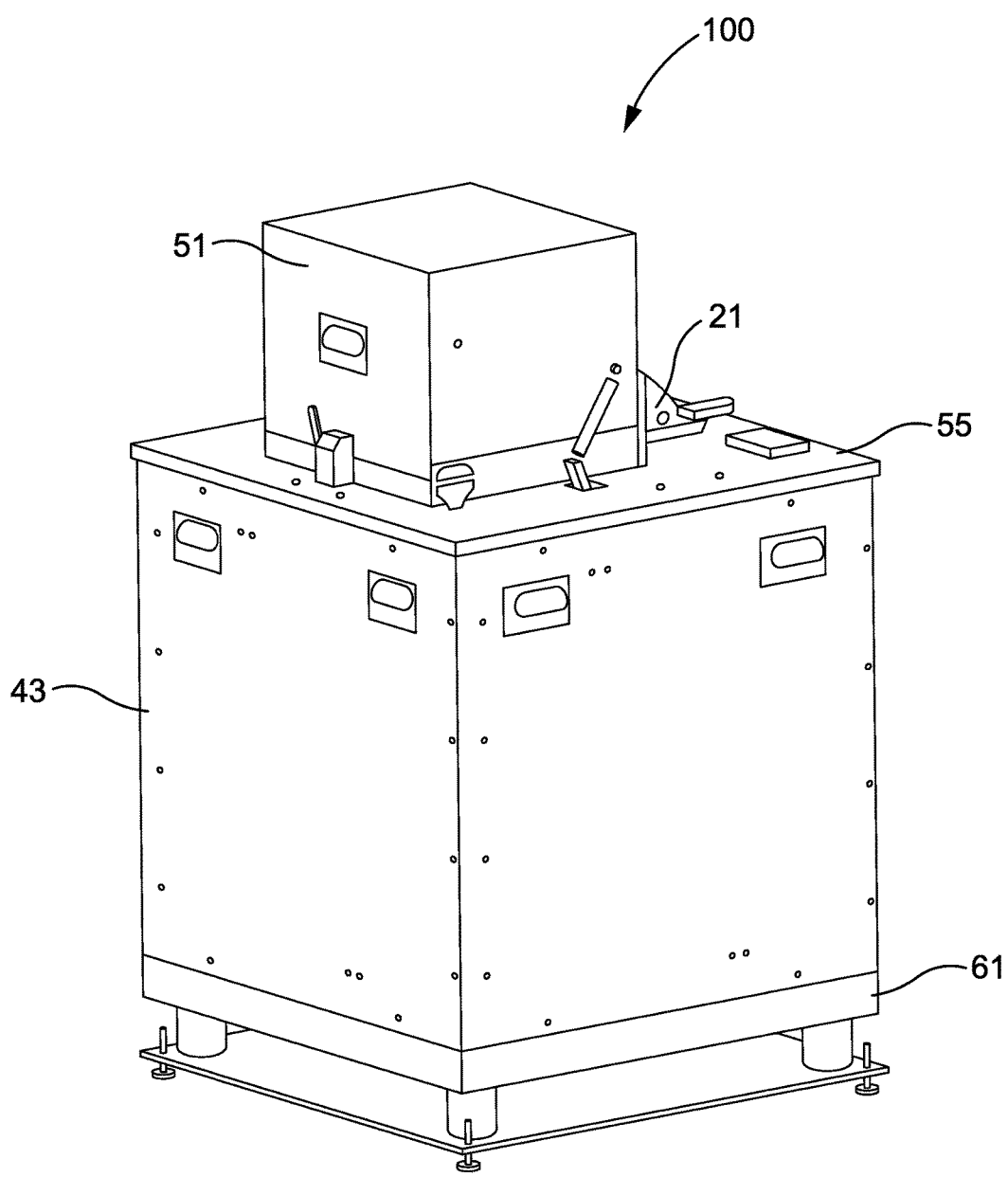
FIG. 1 shows a microscope with high spatial and temporal resolution for imaging dynamic processes.

The invention provides an open-stage microscope for illuminating a sample with near-TIRF light in a configuration that allows living cells to be observed and imaged. The invention is particularly useful for observing fluorescence in biological moieties with rapid dynamics and fluorophores having low quantum efficiency. The microscope illuminates the sample from the side rather than through the objective lens, which allows more intense illumination, and a corresponding lower numerical aperture and larger field of view. By using illumination light at a wavelength distinct from the wavelength of fluorescence, the open-stage TIRF microscope allows the illumination to be nearly completely removed from the image with optical filters, resulting in images that have a dark background with bright areas of interest. The microscope can observe fluorescence to provide indicative measures of underlying chemical or biochemical processes, for example the expression of a gene, the presence of an antibody, or the location of specific proteins within a cell.

Fluorescent reporters such as QuasAr2 and QuasAr3 require intense light in order to fluoresce. Low quantum efficiency and rapid dynamics demand intense light to measure electrical potentials. The illumination subsystem is therefore configured to emit light at high wattage or high intensity. Characteristics of a fluorophore such as quantum efficiency and peak excitation wavelength change in response to their environment. The intense illumination allows that to be detected. Autofluorescence caused by the intense light is minimized by the microscope in multiple ways. The use of near-TIRF illumination exposes only a small portion of the sample to the illumination light, thereby reducing excitation of the culture medium or other components of the device. Additionally, the microscope is configured to provide illumination light that is distinct from imaging light. Optical filters in the imaging subsystem filter out illumination light, removing unwanted fluorescence from the image.

The near-TIRF microscope is configured to optically characterize the dynamic properties of cells. The microscope realizes the full potential of all-optical characterization by simultaneously achieving: 1) a large field of view (FOV) to allow measurement of interactions between cells in a network or to measure many cells concurrently for high throughput; 2) high spatial resolution to detect the morphologies of individual cells and facilitate selectivity in signal processing; 3) high temporal resolution to distinguish individual action potentials; and 4) a high signal to noise ratio to facilitate accurate data analysis. The microscope can provide a field of view sufficient to capture tens or hundreds of cells. The microscope and associated computer system provides a very fast image acquisition rate on the order of 1 kilohertz, which corresponds to a very short exposure time on the order of 1 millisecond, thereby making it possible to record the rapid changes that occur in electrically active cells such as neurons. The microscope can therefore acquire fluorescent images using the recited optics over a substantially shorter time period than prior art microscopes.

The microscope achieves all of those demanding requirements to facilitate optically characterizing the dynamic properties of cells. The microscope provides a large FOV with sufficient resolution and light gathering capacity with a low numerical aperture (NA) objective lens. The microscope can image with magnification in the range of 2× to 6× with high-speed detectors such as sCMOS cameras. The microscope further provides a numerical aperture of approximately 0.4 to 1.0 to achieve the required spatial and temporal resolution. To achieve fast imaging rates, the microscope uses extremely intense illumination, typically with fluence greater than 50 W/cm2 at a wavelength of about 635 nm up to about 2,000 W/cm2.

Despite the high power levels, the microscope nevertheless avoids exciting nonspecific background fluorescence in the sample, the cell growth medium, the index matching fluid, and the sample container. Near-TIRF illumination limits the autofluorescence of unwanted areas of the sample and sample medium. Optical filters in the imaging subsystem prevent unwanted light from reaching the imager. Additionally, the microscope prevents unwanted autofluorescence of the glass elements in the objective lens by illuminating the sample from the side, rather than passing the illumination light through the objective unit. The objective lens of the microscope may be physically large, having a front aperture of at least 50 mm and a length of at least 100 mm, and containing numerous glass elements.

The microscope can be used to observe fluorescent indicators that are sensitive to specific physical properties of their environment such as calcium ion concentration or membrane potential. The time-varying signal produced by these indicators is repeatedly measured to chart the course of chemical or electronic states of a living cell. One example of an environmentally sensitive fluorescent indicator for use with the present invention is the archaerhodopsin-based protein QuasAr2, which is excited by red light and produces a signal that varies in intensity as a function of cellular membrane potential. QuasAr2 can be introduced into cells using genetic engineering techniques such as transfection or electroporation, facilitating optical measurements of membrane potential.

In addition to fluorescent indicators, open-stage near-TIRF microscopes can be used to optically activate light-sensitive compounds for chemically or electrically perturbing cells. The invention can be used with voltage-indicating proteins such as those disclosed in U.S. Patent Publication 2014/0295413, filed Jun. 12, 2014, the entire contents of which are incorporated herein by reference. Using light-controlled activators, stimulus can be applied to entire samples, selected regions, or individual cells by varying the illumination pattern. One example of a light-controlled activator is the channel rhodopsin protein CheRiff, which produces a current of increasing magnitude roughly in proportion to the intensity of blue light falling on it. In one study, CheRiff generated a current of about 1 nA in whole cells expressing the protein when illuminated by about 22 mW/cm2 of blue light.

Optically modulated activators can be combined with fluorescent indicators to enable all-optical characterization of specific cell traits such as excitability. For example, a channel rhodopsin such as CheRiff is combined with a fluorescent indicator such as QuasAr2. The microscope provides different wavelengths of light to illuminate and activate the reporter and activator proteins, respectively, allowing membrane potential to be measured at the same time that action potentials are initiated by light.

Samples useful with the near-TIRF microscope include cells expressing an optical activator of electrical activity and an optical reporter of electrical activity. The sample may be configured such that a first cell expresses the activator and a second cell expresses the reporter. The microscope can activate the light-sensitive activator protein with an activation beam to cause a conformational change in the protein, thereby initiating a change in membrane potential in the cell. The result is that the cell "fires," i.e., an action potential propagates in the electrically-active cell. The microscope can simultaneously illuminate a fluorescent optical reporter protein with an illumination beam that is spectrally distinct from the activation beam, causing the reporter to fluoresce. The imaging subsystem of the microscope can measure the fluorescence emitted by the reporter to measure corresponding changes in membrane potential.

The near-TIRF microscope employs numerous light subsystems. All embodiments include at least an illumination light subsystem for exciting a reporter protein and an imaging light subsystem to image the light emitted by the reporter. The microscope may also include an activation light subsystem for activating an activator protein such as a light-gated ion channel. For the sake of clarity, the illumination subsystem refers to a subsystem for emitting illumination light for energizing a reporter protein so that it can fluoresce upon a change in action potential. The imaging subsystem refers to a subsystem for receiving the light emitted by the reporters when they fluoresce, and the light that they emit is referred to as imaging light. The activation subsystem refers to the subsystem that emits light for activating a light-gated ion channel protein for initiating change in membrane potential.

FIG. 1 shows a microscope 100 with high spatial and temporal resolution for imaging dynamic processes. The microscope 100 may be used in conjunction with fluorescence imaging wherein the fluorescence may be mediated by voltage-indicating proteins to measure the electrical properties of cells. The microscope 100 may also be used with light-sensitive activators to allow selective, variable intensity activation of cells. The improved systems for optical electrophysiology measurements disclosed herein will allow researchers to more productively study electrically excitable cells such as neurons and cardiomyocytes, thereby providing new insights into heart and brain diseases, leading to treatments and cures. Components of the invention include a large FOV, high-resolution imaging subsystem; an illumination subsystem; an optional activation subsystem; and a sample positioning and environmental control subsystem. Microscope 100 may be used to image and illuminate living cells that express optogenetic proteins. As shown in FIG. 1, microscope 100 includes a sample enclosure 51 serviced by an environmental control system 21. A top platform 55 is supported above side walls 43 and base platform 61. The environmental control system 21 is part of the overall sample handling system. This provides control over humidity, temperature, gas, and sample positioning.

Figure 2:
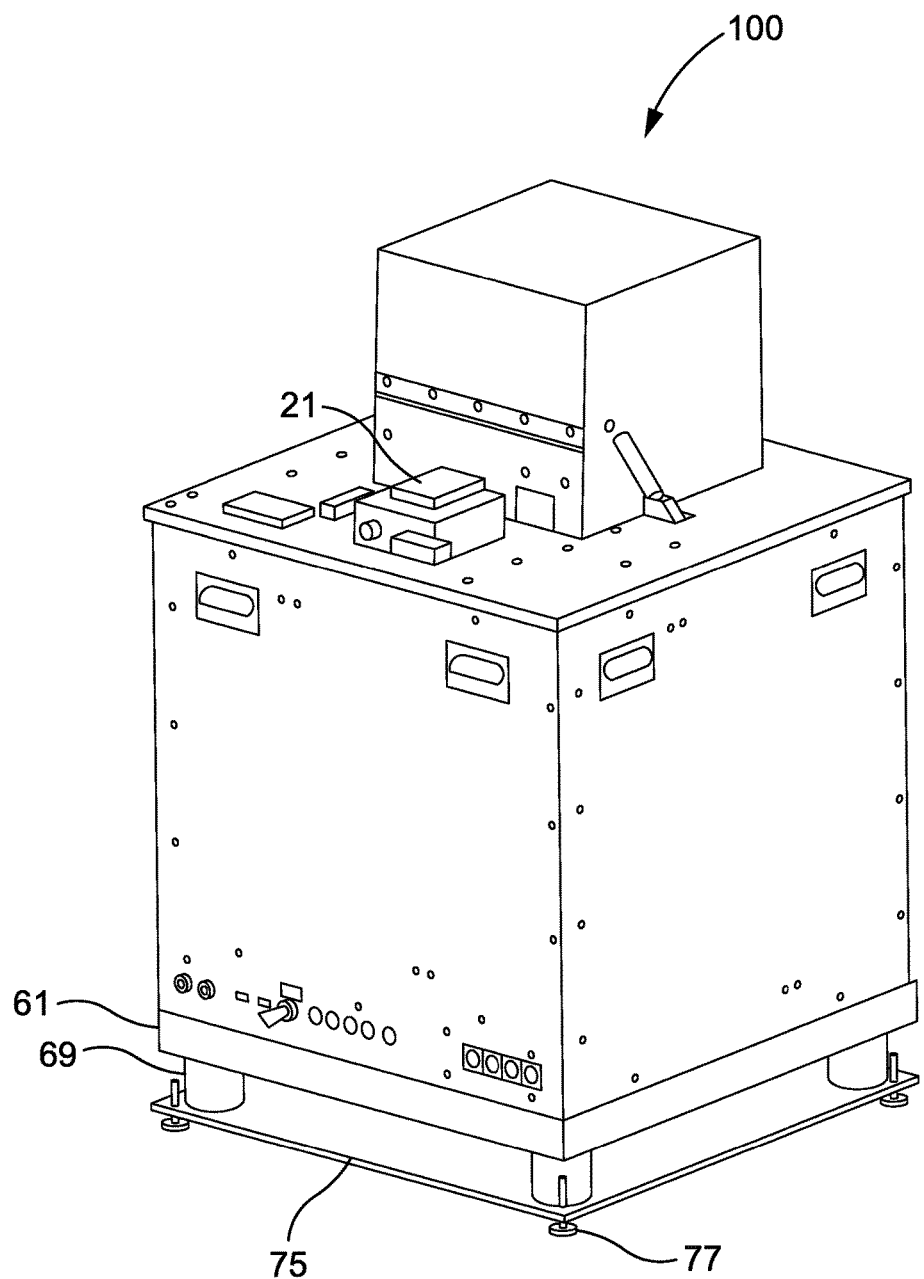
FIG. 2 shows another view of the microscope of FIG. 1.

FIG. 2 shows base platform 61 supported by supports 69 on lower platform 75, which employs leveling feet 77. The feet 77 can be used to level the sample stage 109 (shown in FIG. 4). Because the open-stage microscope provides a sample stage configured to contain samples including aqueous solutions, it is important to ensure the stage is level. The feet can include a screw portion engaged with a threaded hole in the lower platform 75. The feet 77 can be adjusted by turning their respective screws. The supports 69 are slightly inset from the location of the feet 77, thereby providing access for the feet 77 to be adjusted by a human operator. The base platform 61 and lower platform 75 should be substantially flat and made from a resilient material such as aluminum or steel. The feet 77 and supports 69 should likewise be manufactured from a resilient material capable of withstanding the weight of the microscope and all of its components.

Figure 3:
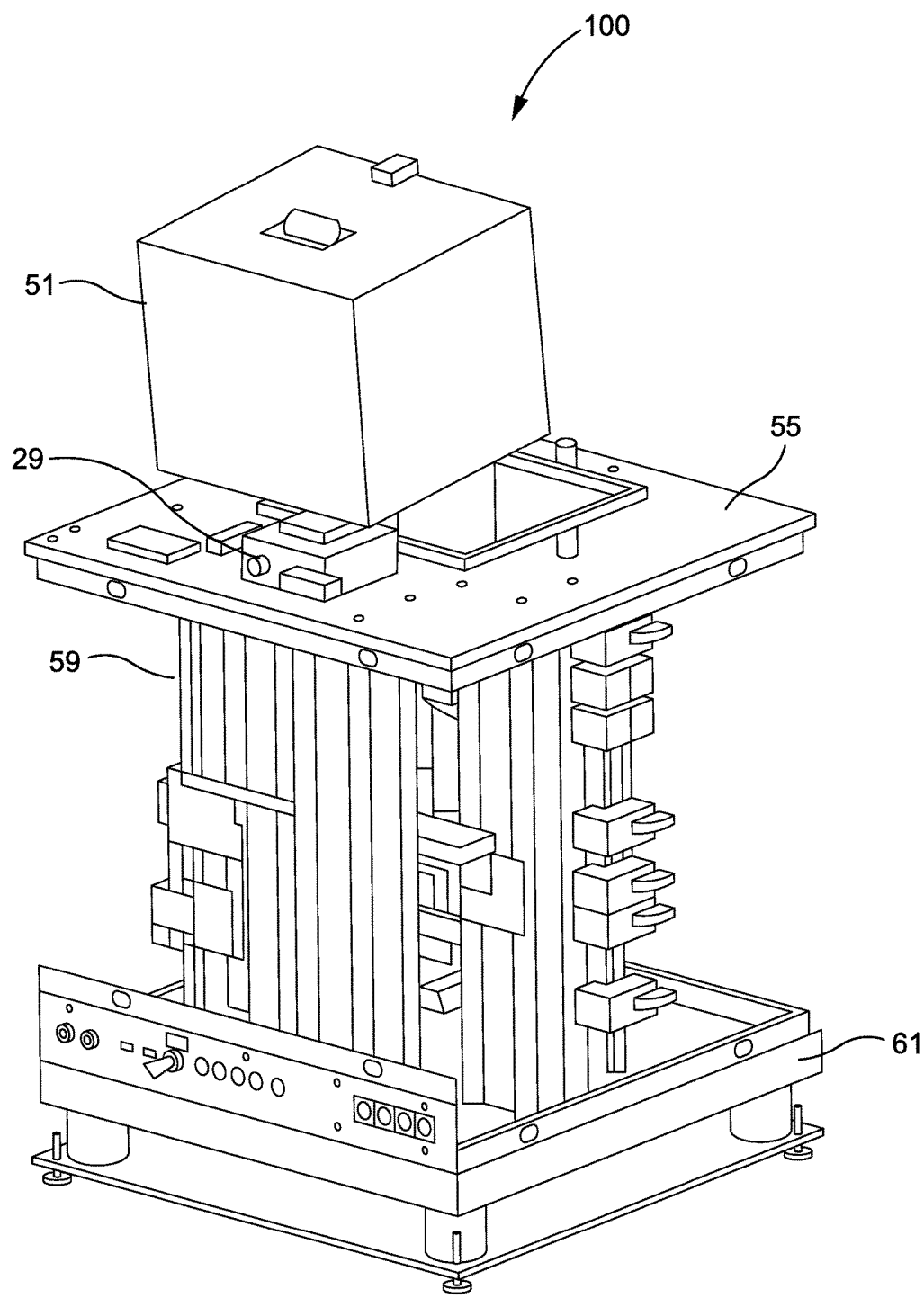
FIG. 3 shows another view of the microscope of FIG. 1 with side walls removed.

FIG. 3 gives a back perspective view of microscope 100 with the side walls 43 removed. As shown, top platform 55 is supported by uprights 59. Each upright 59 is preferably an extended rail of metal or a polymer that rigidly supports top platform 55 above base platform 61. The components of the optical subsystems—described in greater detail below— may be mounted to the uprights 59. The uprights 59, top platform 55, and base platform 61 cooperate to define a chassis for supporting the illumination and imaging subsystems. Additionally, top platform 55 and base platform 61 may include mounting flanges (e.g., with threaded holes) to which side walls 43 can be affixed, thus provided a dark enclosure within which the optical elements of the microscope can be housed and operate. A sample positioning system 29 is installed in top platform 55. The sample positioning system 29 can be used to adjust the object region 109 (shown in FIG. 4) up, down, left, right, forward, and backwards. It can also adjust the tilt of the object region and it can rotate the sample.

Figure 4:
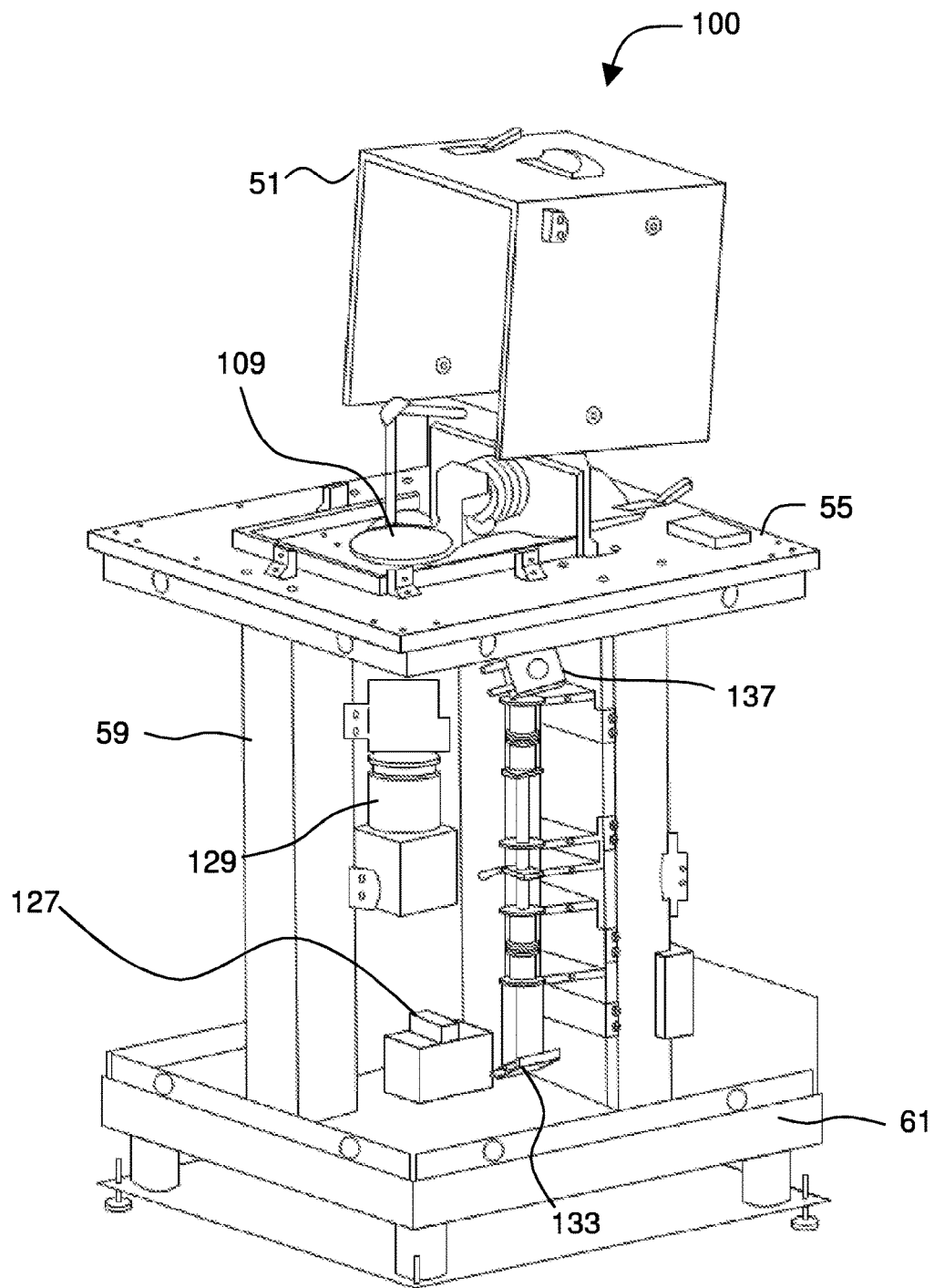
FIG. 4 shows another view of the microscope of FIG. 1 with the object region visible.

FIG. 4 gives a front perspective view of microscope 100 with the side walls removed. It can be seen that sample enclosure 51 can be used to enclose sample stage 109. One or more illumination light sources 127 can be included among the components beneath the sample stage.

The sample stage 109 is supported above an objective lens unit 129. Components of an illumination subsystem are also shown mounted to uprights 59. The illumination subsystem includes an illumination light source 127 (e.g., a red diode laser bar), a mirror 133 and an adjustable mirror 137, which can be adjusted manually or by way of a stepper motor or translation motor.

Figure 5:
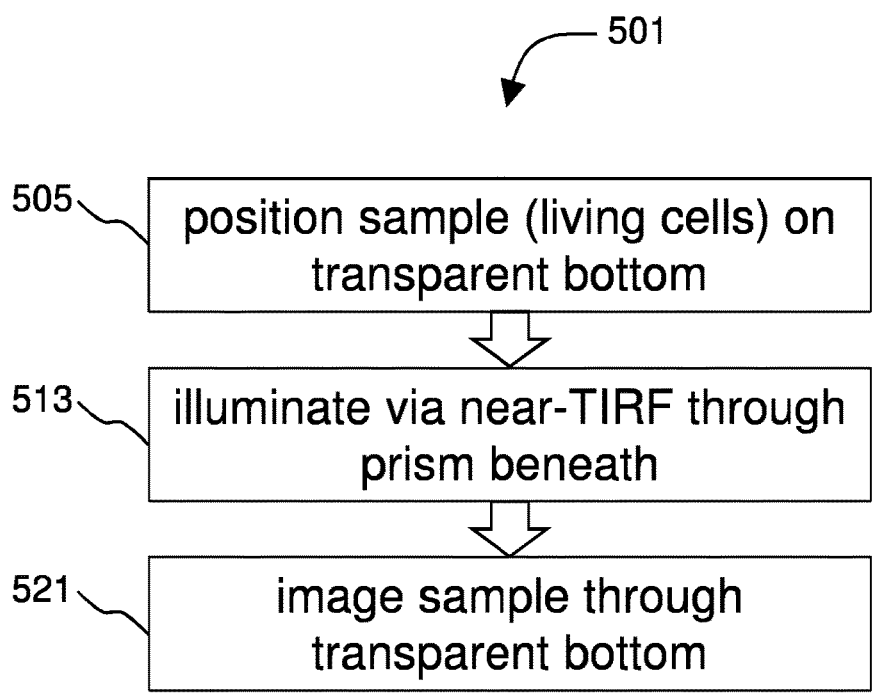
FIG. 5 diagrams methods of the invention.

FIG. 5 diagrams a method 501 for imaging a sample. The method 501 includes the steps of positioning 505 a sample dish 111 in an object region 109 of a stage of a fluorescence microscope 100, wherein the sample dish 111 comprises a transparent bottom portion 112 and contains a biological sample (e.g., cells 113) in an aqueous medium 138; illuminating 513 the biological sample from beneath via an illumination light 135 passing through a prism 125 disposed underneath the transparent bottom portion, whereby the prism 125 imparts near total internal reflection on the illumination light; and imaging 521 the biological sample through the transparent bottom portion using an imaging subsystem 191 of the microscope 100, the imaging subsystem 191 comprising an objective lens unit 129 disposed beneath the sample dish 111 and an image capture device 197. Preferably, the prism and transparent bottom portion are coupled by a low-autofluorescence index matching fluid; and the prism, the index matching fluid, and the transparent bottom portion have a common index of reflection. The sample dish can provide access to the sample from above. The method 501 may include using an environmental control subsystem to control environmental conditions above the aqueous medium to maintain living cells 113 in the aqueous medium. As discussed elsewhere herein, the environmental control subsystem may control humidity, temperature, or gas of the sample region. The transparent bottom portion of the sample dish may be provided by a coverslip mounted to a surrounding dish structure.

The method 501 may include transmitting an activation light onto the sample using an activation subsystem comprising an activation light source (e.g., diode laser bar, diode laser, or LED), wherein the activation light is spectrally distinct from the illumination light.

Preferably, the activation subsystem transmits the activation light upwards through the objective lens unit and onto the sample. The method 501 may include focusing the activation light at a back aperture of the objective lens using an activation tube lens disposed within a path defined by the activation light. The activation subsystem may be operable to spatially pattern the activation light onto the sample (e.g., the activation subsystem may include a spatial light modulator such as a digital micromirror device (DMD); a digital light processor; or a liquid crystal display to spatially pattern the activation light). The spatial light modulator may be controlled by a computer that may define an illumination patter.

The illumination pattern may be generated by the computer based on an input from the imaging subsystem. For example, the input from the imaging subsystem may include a pattern of one or more cells 113 in the sample. In some embodiments, the computer defines an illumination pattern with the spatial light modulator that corresponds to the pattern of cells in the sample, thereby causing the activation subsystem to transmit illumination light onto the one or more cells. The method 501 may include reflecting the activation light upwards onto the sample using a dichroic mirror, and allowing the image to pass downward through the dichroic mirror to the image capture device. In some embodiments, the activation light has a wavelength capable of activating a light-sensitive activator protein. The light-sensitive activator protein may be a light-gated ion channel with the wavelength being between 450 and 495 nm. In certain embodiments of the method 501, the illumination light has a wavelength capable of illuminating a microbial rhodopsin, e.g., between 580 and 650 nm.

The method 501 may include using baffles to block unwanted reflected light from entering the objecting lens. Preferably, the objective lens has a numerical aperture between 0.4 and 1.0—e.g., about 0.5. In certain embodiments, the image capture device 197 is a camera such as a CMOS camera with a field of view sufficient to capture between one and five hundred cells. The image capture device may acquire images at 1 kHz, preferably with a minimum exposure time of the camera is 1 ms or less. The method 501 may further include transmitting a second illumination light onto the sample, e.g., a wavelength capable of illuminating a light-sensitive reporter protein such as a calcium-indicating protein.

Figure 6:
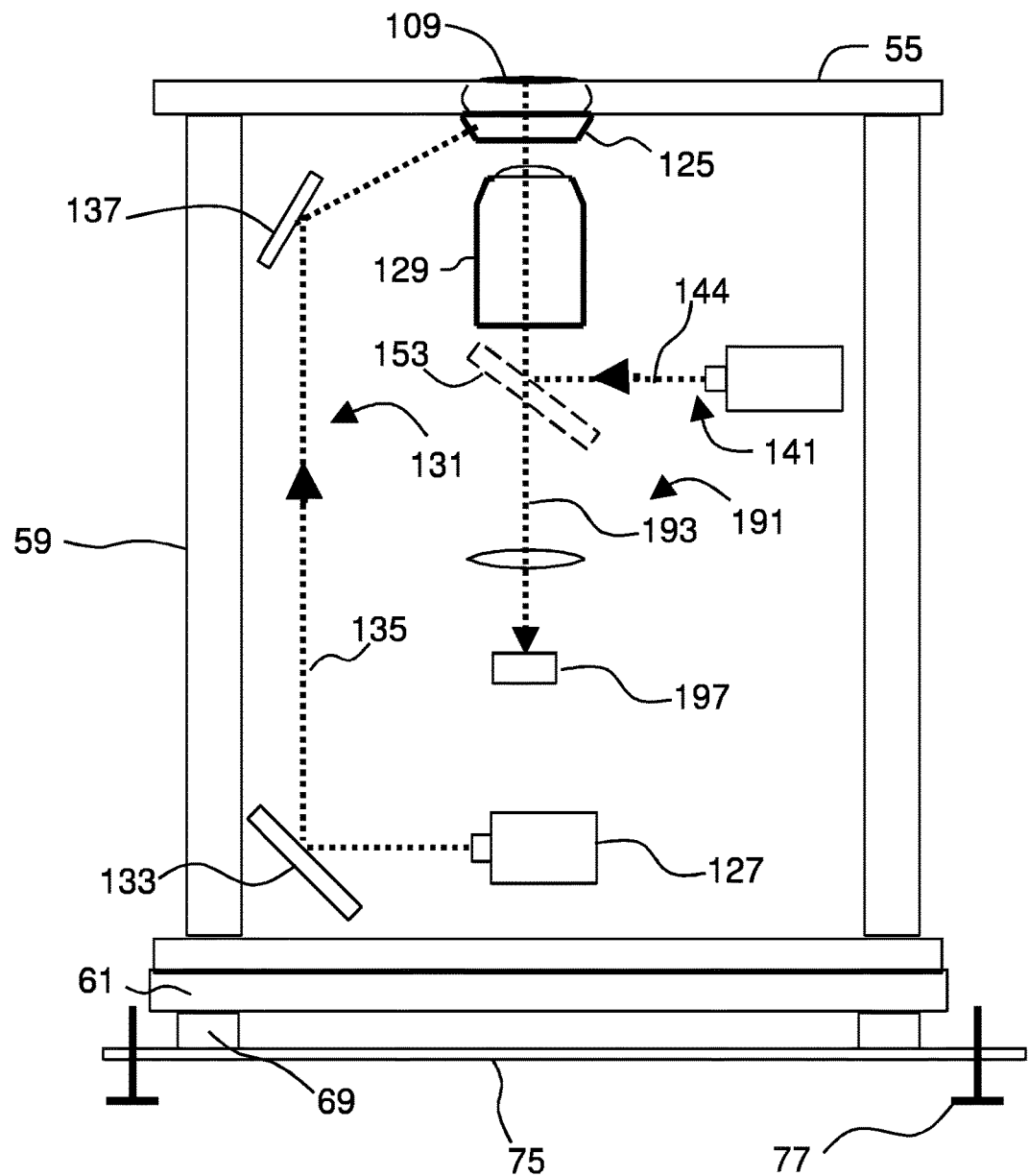
FIG. 6 is a schematic view showing how the illumination subsystem, the imaging subsystem, and the activation subsystem may be disposed within the microscope.

FIG. 6 illustrates an embodiment of how the illumination subsystem 131, the imaging subsystem 191, and the activation subsystem 141 are disposed within device 100. For illumination subsystem 131, an illumination light source 127 generates illumination light 135 which via stepper/translator mirrors 133 and 137 impinges on a prism 125. For the activation subsystem 141, activation light 144 is reflected off of dichroic mirror 153 and then passed through the objective unit 129, after which it impinges upon a sample in sample stage 109. In the imaging subsystem 191, image light 193 passes from the sample stage 109 through the objective unit 129 and through the dichroic mirror 153 to camera or light detector 197. The operation of these subsystems is described in greater detail below.

Figure 7:
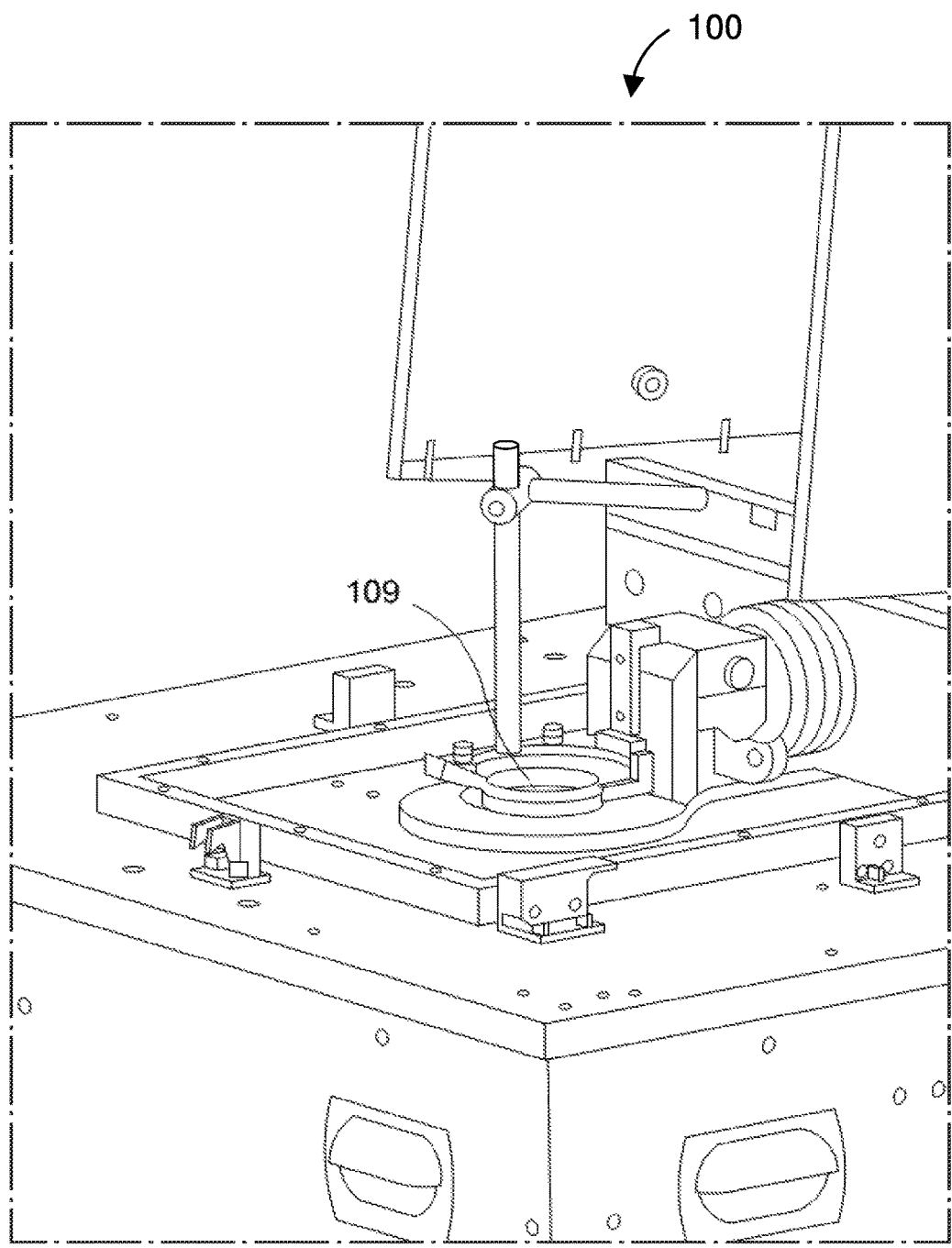
FIG. 7 shows a close-up view of the sample stage and object region

FIG. 7 gives a close-up view of sample stage/object region 109 of the system 100. The object region 109 is configured for holding a sample to be observed. The object region 109 is located within an imaging optical path of the microscope. It is important to note that any sample loaded into sample stage 109 can be open in an upward direction. That is, microscope 100 does not require any optical instrumentation or objects to touch, enclose, or impinge upon a sample being investigated. The enclosure 51 may be closed and latched closed to minimize unwanted interference from outside light, but microscope 100 still provides generous open space above sample stage 109. In fact, sample stage 109 may include cells in an aqueous medium such as a maintenance broth. Since the sample container may be open-topped, microscope 100 allows for direct stimulation of the sample (e.g., physical stimulation, contact by electrodes, etc.).

Devices and methods of the invention may be used to exploit fluorescent indicators that are sensitive to specific physical properties of their environment such as calcium ion concentration or membrane potential. The time-varying signal produced by these indicators can be repeatedly measured to chart the course of chemical or electronic states of a living cell. One example of an environmentally sensitive fluorescent indicator is the archaerhodopsin-based protein QuasAr2, which is excited by red light and produces a signal that varies in intensity as a function of cellular membrane potential. QuasAr2 can be introduced into cells using genetic engineering techniques such as transfection or electroporation, facilitating optical measurements of membrane potential.

The invention provides in a large FOV optical microscope 100 that may be used to simultaneously image dozens, hundreds, or even thousands of cells. Since so many cells may be simultaneously imaged, optical characterization of cellular membrane potential can increase throughput by many orders of magnitude.

To realize the full potential of all-optical characterization, a microscope 100 may be used for simultaneously achieving a large FOV to allow measurement of interactions between cells in a network or to measure many cells concurrently for high throughput; high spatial resolution to detect the morphologies of individual cells and facilitate selectivity in signal processing; high temporal resolution to distinguish individual action potentials; and a high signal to noise ratio to facilitate accurate data analysis. The FOV is preferably sufficiently large to capture dozens or hundreds of cells, with a resolution on the order of 1 or 2 microns. To record the rapid changes that occur in electrically active cells such as neurons, microscope 100 can provide a very fast image acquisition rate on the order of 1 kilohertz, which corresponds to a very short exposure time on the order of 1 millisecond. (Most fluorescent images are acquired over a substantially longer time period.) The confluence of the above requirements places extreme demands on instruments for optically characterizing the dynamic properties of cells.

The microscope 100 provides a large FOV with sufficient resolution and light gathering capacity using a low magnification, low numerical aperture (NA) objective lens in objective unit 129. An optical system with magnification in the range of 2× to 6× is typically required for imaging with contemporary high-speed detectors such as a sCMOS camera 197. A numerical aperture 0.4 to 1.0, and preferably about 0.5, achieves the required spatial and temporal resolution. Objective lenses with these characteristics are physically quite large, typically with a front aperture of at least 50 mm and a length of at least 100 mm, and they contain numerous glass elements. Fast imaging rates necessitate the use of extremely intense illumination, typically with fluorescence greater than 50 W/cm2 at a wavelength of about 635 nm up to about 2,000 W/cm2.

Illuminating such a large FOV with high intensity requires a high-power source. For example, achieving 200 W/cm2 over an area of 1 mm×3 mm requires a total power of 6 W. That is much more power than is typically used in fluorescence microscopy. Intense illumination tends to excite non-specific background fluorescence of the sample, optical elements of the microscope, cell growth medium, index matching fluids, and sample container. As such, it is not practical to illuminate the sample through the objective as is commonly done in epifluorescence microscopy and special measures must be taken to reduce background fluorescence. Passing so much power through the large number of glass elements contained inside the objective lens induces autofluorescence in the glass of sufficient magnitude to obscure the weak fluorescence signal emitted by the sample.

One method for reducing background fluorescence, for example the intrinsic fluorescence of the culture medium, is to use total internal reflection fluorescence (TIRF) microscopy.

Figure 8:
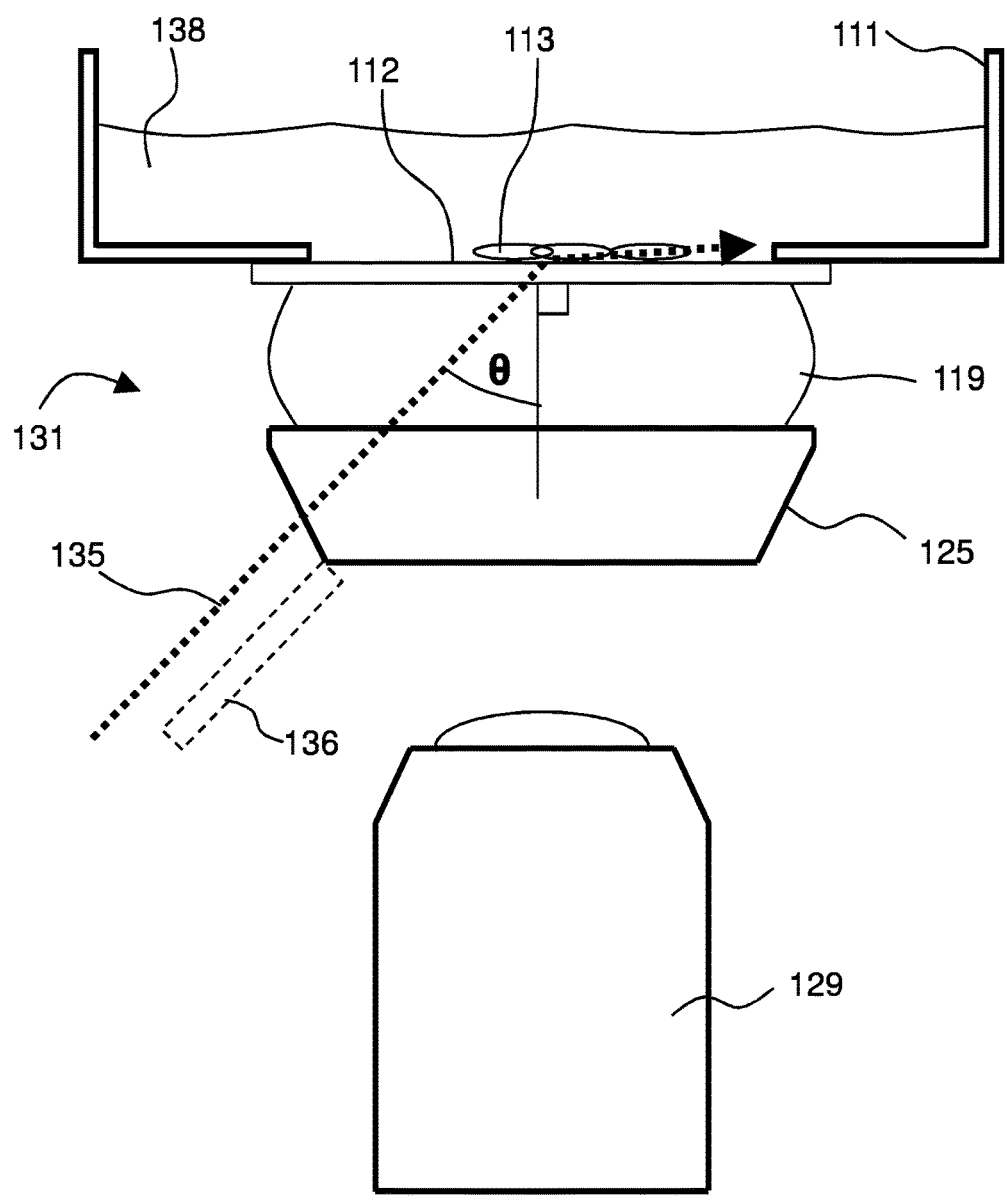
FIG. 8 shows a detailed view of part of the illumination subsystem including a prism.

FIG. 8 shows a detail view of part of the illumination subsystem 131. Here, sample dish 111 defines or sits in sample stage 109. A glass coverslip 112 is cemented into dish 111. Dish 111 may include an aqueous medium 138 such as a maintenance broth for cells. In the depicted embodiment, one or more cells 113 are growing on coverslip 112. A prism 125 is situated beneath the coverslip and the space between the prism 125 and the coverslip 112 is filled with index matching fluid 119. In some embodiments, the prism 125, the coverslip 112, and the index matching fluid 119 all have the same index of refraction so that the illumination light 135 does not refract at any of the phase changes or materials boundaries between those objects. In some embodiments, the refractive indices are close, but not identical. For example, it may be advantageous to use a material that is very pure but has a refractive index that is not an exact match. In some embodiments cells are grown directly on a prism, thereby obviating the need for the coverslip or index matching fluid.

As illustrated in FIG. 8, the illumination light 135 impinges upon a top surface of the coverslip 112 at an angle θ with the normal to that top surface of the coverslip. By setting θ very close to the angle of total internal reflection (TIRF), excellent illumination of a thin layer of cells 113 is achieved.

Near-TIRF confines the illumination to a thin region of the sample in the vicinity of the coverslip 112. That region, however, is greater than the region that would be illuminated with traditional TIRF. In the depicted configuration, the illumination light 135 is coupled to the sample 113 by a prism 125. In prior art TIRF microscopy, the sample resides in a thin flow-chamber with the objective lens on one side of the sample and the light-coupling prism is on the opposite side of the sample. A drawback of that prior art TIRF implementation is the requirement that the sample be contained in a flow-chamber, which is incompatible with many cell-culture techniques such as glass bottom culture dishes and well plates. Another drawback is that the optical elements on both sides of the sample interfere with physical access to the sample. Furthermore, TIRF only illuminates a region of approximately a few hundred nanometers. Near-TIRF, however, illuminates a region on the order of 10 microns, and so it can illuminate a whole cell rather than just a small portion of a cell.

In addition to fluorescent indicators, light-sensitive compounds have been developed to chemically or electrically perturb cells. Using light-controlled activators, stimulus can be applied to entire samples, selected regions, or individual cells by varying the illumination pattern. One example of a light-controlled activator is the channel rhodopsin protein CheRiff, which produces a current of increasing magnitude roughly in proportion to the intensity of blue light falling on it. In one study, CheRiff generated a current of about 1 nA in whole cells expressing the protein when illuminated by about 22 mW/cm2 of blue light.

Optically modulated activators can be combined with fluorescent indicators to enable all-optical characterization of specific cell traits such as excitability. For example, the OptoPatch method combines an electrical activator protein such as CheRiff with a fluorescent indicator such as QuasAr2. The activator and indicator proteins respond to different wavelengths of light, allowing membrane potential to be measured at the same time cells are excited over a range of photocurrent magnitudes.

Measuring the electrical properties of cells is of primary importance to the study, diagnosis, and cure of diseases that involve electrically active cells, such as heart and brain cells (neurons and cardiomyocytes). Conditions that affect these cells include heart disease, atrial fibrillation, amyotrophic lateral sclerosis, primary lateral sclerosis, and many others. All-optical measurements provide an attractive alternative to conventional methods like patch clamping because they do not require precise micromechanical manipulations or direct contact with cells in the sample. Optical methods are much more amenable to high-throughput applications. The dramatic increases in throughput afforded by all-optical measurements have the potential to revolutionize study, diagnosis, and treatment of these conditions.

In various aspects, the present invention is generally directed to characterizing the physical properties of cells using fluorescent indicators and light-sensitive activators. Examples of applications of the system include studying the effect of a potential drug compound on cardiomyocytes. For example, the microscope could be used to optically obtain an action potential (AP) and calcium transient (CT) waveform from a stem-cell derived cardiomyocyte to characterize an arrhythmia in the cardiomyocyte. A cardiomyocyte in the sample could be caused to express a rhodopsin-type transmembrane optical reporter. The microscope can activate a microbial channel rhodopsin using the activation subsystem. An AP propagates through the cardiomyocyte. A cell containing a reporter protein is illuminated via the illumination subsystem, and the AP causes a change in the fluorescence of the reporter. Light from the reporter is detected by the imaging subsystem and analyzed to construct the AP waveform. An arrhythmia in the constructed AP waveform can be detected or characterized, e.g., by comparison to a known standard or other analytical techniques.

The near-TIRF microscope can thus be used to study a compound's effect on cardiomyocytes. Because the object region can support a cell in a medium, a sample cardiomyocyte can be observed with the microscope while exposed to a compound of interest, such as a prospective drug. Any resulting perturbation to the detected AP waveform, or arrhythmia, associated with exposure to the compound can thus be observed by the microscope. Since the optical reporter can include a voltage reporter, an ion reporter (e.g., for [Ca2+]), others, or combinations thereof, the microscope can detect the effect of the compound across multiple ion channels of the cardiomyocyte as revealed through all features of the AP waveform.

Figure 9:
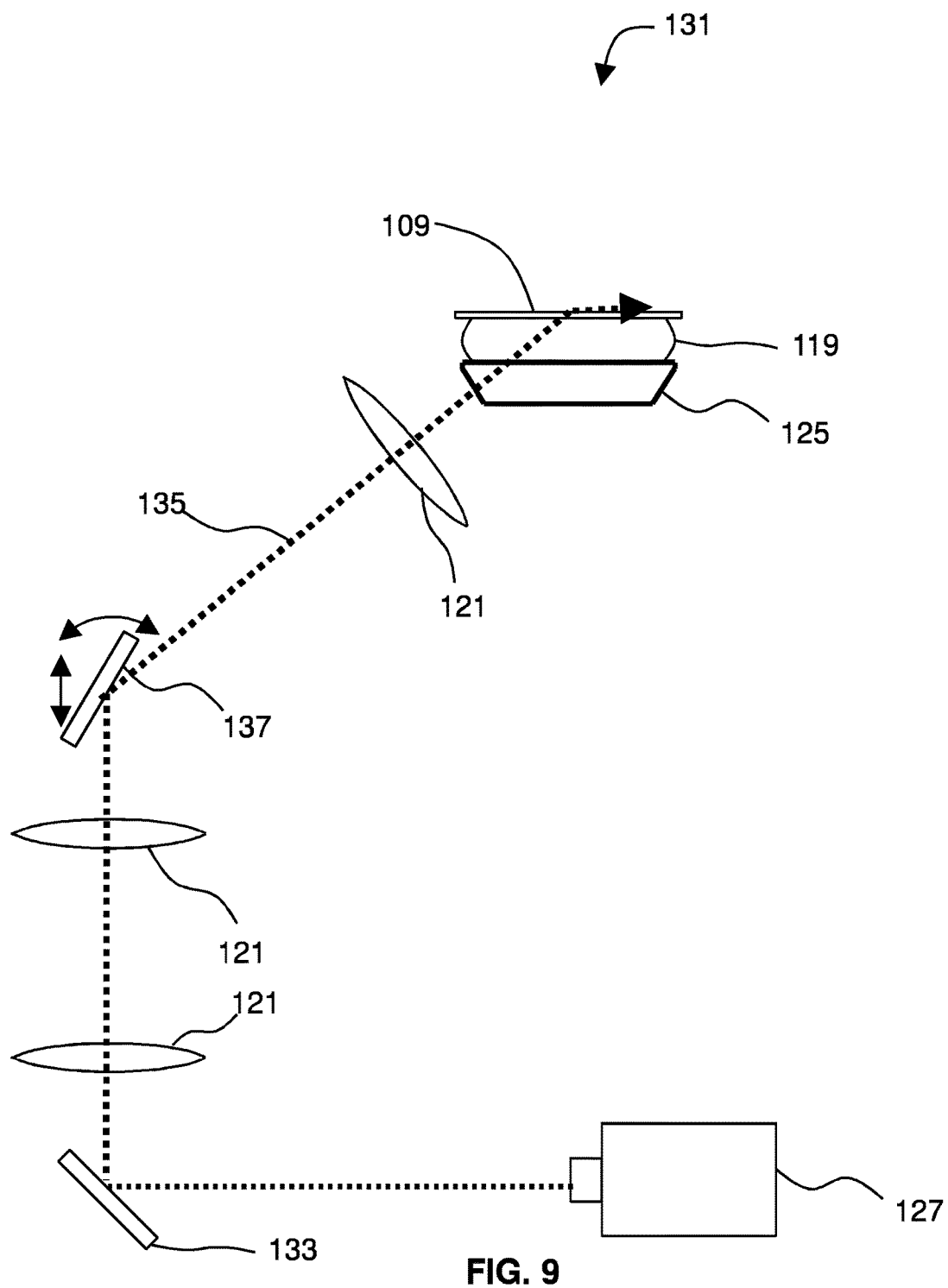
FIG. 9 shows an illumination subsystem of the present disclosure.

FIG. 9 illustrates components of the illumination subsystem 131. Light source 127 provides illumination light 135 of suitable power and wavelength to excite fluorescent indicators in the sample. One example light source is a diode bar laser part number MB-638.3-8C-T25-SS4.3 manufactured by Dilas Corporation. This particular laser provides up to about 9 W of power with a rectangular beam profile at a wavelength of approximately 638 nm. Other sources could be used in the illuminator.

Laser bars for illuminating the sample may be configured with a propagation axis that is not co-axial with the illumination path. The laser bars may provide light to the illumination optical path at a wavelength corresponding to an activation wavelength of a protein found in the sample, such as a red wavelength between 580 and 650 nm used to excite fluorescence of a microbial rhodopsin.

FIG. 9 depicts on suitable configuration for use in the illumination subsystem 131. As shown in FIG. 9, cylindrical lens 121 is placed one focal length from the laser with its optical axis orientated to coincide with the fast propagation axis of the beam. Mirror 133 deflects the beam upward. Lenses 121 produce a homogenized beam one focal length farther down the optical path of the illuminator and relay the beam to the sample plane. Additionally, other beam shaping optics may be disposed within the illumination path.

An adjustable mirror 137 is placed in a kinematic translation/tip/tilt mount located near the focal point of relay lens 121. This allows the position and incidence angle to be independently adjusted. The adjustable mirror 137 can be adjusted manually, or in other embodiments can be adjusted by way of a stepper motor or translation motor. Prism 125 couples the illumination to the sample stage 109 via index matching fluid 119. This arrangement allows physical access to the sample from the top and avoids passing high-power illumination through the objective. The index matching fluid 119 may be selected to minimize autofluorescence, for example Type FF microscope oil manufactured by Cargille Corporation or ultra-pure glycerol. The side of the prism facing the objective may be given an anti-reflective coating to facilitate improved transmission of sample fluorescence.

Prism 125 is preferably made out of a material such as fused silica, selected to have very low auto-fluorescence. The prism preferably does not obstruct the aperture of the objective lens. Furthermore, the prism is thick enough to accommodate the geometry of the illumination beams entering on its side faces at near the TIR angle, but not so thick as to create large optical aberrations. If the prism is too wide, the illumination beams will not be able to reach the sample area. (FIGS. 13A-13C show the geometry of prism 125 in detail.)

The fluorescence illuminator 127 provides light 135 to excite fluorescent indicators in the sample and a means for coupling the light into the sample. It includes one or more light sources of appropriate wavelength and power. Light sources may include diode lasers, diode bar lasers, other types of lasers, LEDs, or other sources with suitable characteristics. Optical filters, mirrors, lenses, prisms, fibers, and other optical elements may be used to alter the spectrum and spatial characteristics of the light source. The coupling means may be a prism and an optional index matching fluid interposed between the objective lens and the sample. The prism may be made of a low autofluorescence material such as fused silica, and the index matching fluid may be specially selected for its low autofluorescence. In this scheme, high power illumination does not pass through the objective lens, thereby reducing nonspecific fluorescence from glass elements of the objective. Illumination is directed at the sample from the side. The illumination may be coupled into the sample at an angle that is near the total internal reflection (TIR) angle in order to minimize background fluorescence from the cell growth medium. The near-TIR angle is exhibited at the interface between the sample support (typically a glass coverslip) and the sample-containing medium (typically an aqueous solution). Illumination may be directed at the sample from multiple directions to further reduce background fluorescence.

FIG. 8 shows a detailed view of light 135 coupling into the sample through prism 125. The diagram shows that more than one illumination beam 135 may be coupled into the sample to further reduce background fluorescence. The beams are adjusted that they strike the glass-water interface at an angle θ close to the TIR angle. The illumination beam may be brought to a focus using a lens of a certain focal length so as to cause Rayleigh length to be approximately equal to the size of the field of view in order to further reduce excitation of background fluorescence. Baffles 136 may be inserted beneath the prism to prevent unwanted ghost images from other facets of the prism from being transmitted into the objective lens.

If the FOV is not square, the illumination is preferably arranged so that the beam propagates parallel to the short axis of the FOV. This arrangement leads to a shorter Rayleigh length than if the beam propagates parallel to the long axis of the FOV. Furthermore, one can arrange two beams to impinge on the FOV from opposite directions. Then each only needs to have a Rayleigh length equal to half the length of the short axis of the FOV. By crossing the beams in the coverslip beneath the sample, one can arrange to minimize auto-fluorescence induced in the cell culture medium.

Systems and methods of the invention provide reduction of the background autofluorescence and unwanted contributions from out-of-focus material near an object to be viewed or imaged. The invention is useful for studying biological processes that utilize voltage-sensitive fluorescent proteins, which can provide a fluorescent signal in response to an electrostatic potential of a cell. Accordingly, spatial and temporal dynamics of time-varying electric potentials can be observed and measured.

The illumination beam 135 of illumination subsystem illuminates the sample cells 113. Where one or more of those cells express an optogenetic indicator such as a microbial rhodopsin, the illumination beam 135 provides the energy to raise electrons in those proteins to an increased energy level. This then allows those proteins to fluoresce on changes in membrane potential, ion concentration, or whatever other phenomenon those proteins report. When the fluorescent reporters (aka indicators) fluoresce, they emit light that is then detected and captured by the imaging subsystem 191 of microscope 100.

Figure 10:
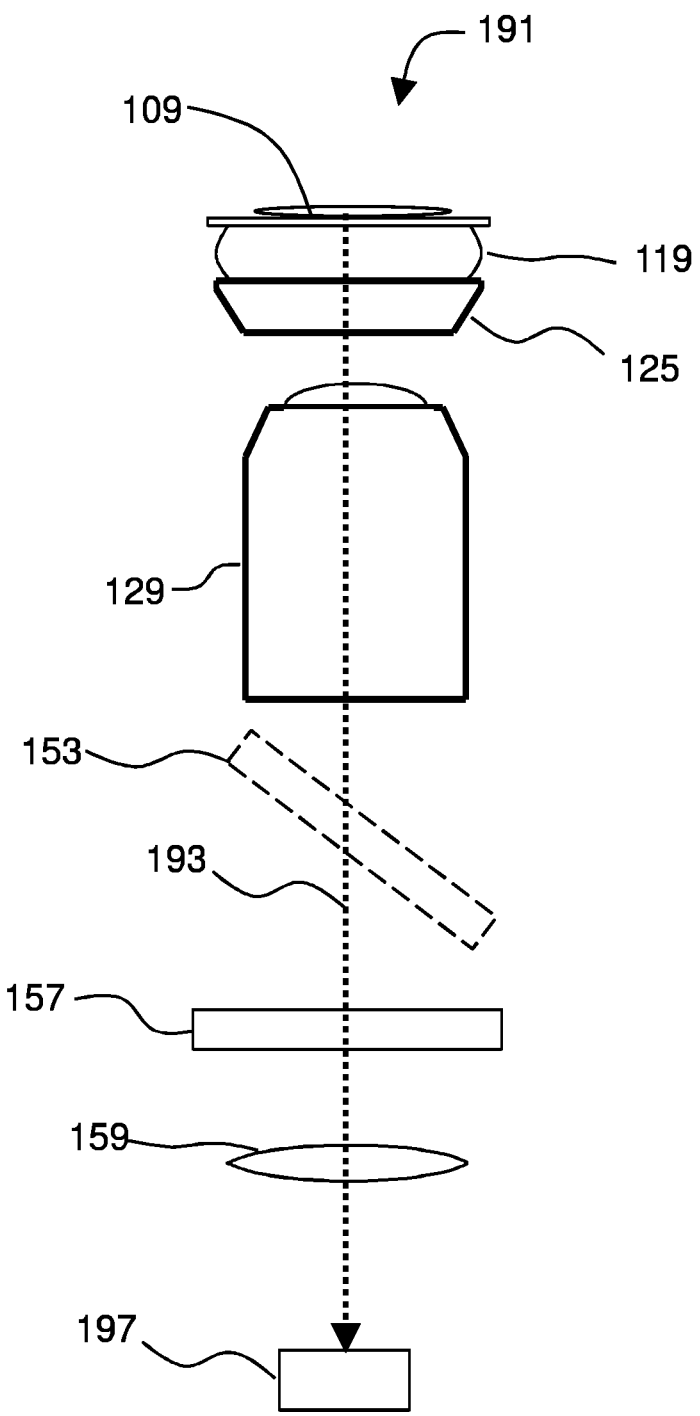
FIG. 10 shows an imaging subsystem of the present disclosure.

FIG. 10 shows details of the imaging subsystem 191. Preferably the imaging light 139 after passing through prism 125 passes through the objective unit 129, an emission filter 157, an imaging tube lens 159 and to light detector/camera 197. The imaging subsystem 191 may include a low magnification, large FOV, high NA objective lens 129; an emission filter 157; a tube lens 159; and an image sensor 197, as shown in FIG. 10. In some embodiments, the imaging light passes through a dichroic mirror 153 that is part of the activation subsystem.

Between the objective lens and the object region 109 is a prism 125. Prisms for use with the invention are shown in greater detail in FIGS. 13A-13C. In a preferred embodiment, the prism 125 has a trapezoidal cross-section with beveled edges. The prism 125 is configured to impart near total internal reflection (TIR) on an illumination beam passing therethrough. Near-TIR excitation serves to limit the production of unwanted fluorescence. The prism and object region 109 are configured such that a user can place index matching fluid 119 between those two elements. In embodiments that include index matching fluid, the near-TIR is exhibited at boundary between the glass coverslip and the aqueous medium 138 containing the sample.

The objective lens 129 preferably has a numerical aperture that is high for lenses of low magnification, for example 0.4, 0.5, 0.6, 0.7, or 0.85. Examples of suitable objective lenses 129 include model number MVPLAPO 2XC manufactured by Olympus Corporation.

The emission filter 157 should exhibit an optical density at the illumination wavelength of at least 5 and preferably greater and transmission of greater than 90% over the emission band. Filters meeting this specification are well known in fluorescence microscopy and are produced routinely by companies such as Semrock Corporation and Chroma Technology. The unique dimensions of the optical path in the present invention require custom sized filters.

The tube lens 159 may be a standard, 3" diameter pianoconvex lens with focal length of 100 mm or it may comprise several elements with a similar equivalent focal length. The choice of 100 mm focal length of the tube lens 159 is matched to the reference tube length of the MVPLAPO 2XC objective (resulting in a magnification of 2×). A different focal length may be selected to achieve larger or smaller magnification. Additional lenses may be added to reduce aberrations.

The image sensor 197 must have sufficient resolution and bandwidth to record signals over the field of view at the desired frame rate. One example of a suitable image detector is a scientific CMOS camera such as the Flash 4.0 sCMOS camera manufactured by Hamamatsu Corporation. Values and specifications of the imaging system components may be adjusted to optimize performance for many circumstances such as a different objective lens, field of view, image sensor, fluorophore, frame rate, or tube lens. The imaging light path may include other optical elements to improve performance.

The system 100 may further comprise additional components to aid in observing and imaging a sample. For example, it may comprise a camera such as a CMOS camera, for obtaining an image from the imaging optical path. The system may also involve a mechanism for adjusting the object region, manually or via computer control, by tilting or translating the object region.

Using the microscope 100, cells 113 or any other suitable sample can be imaged. For example, cells 113 may be neurons, cardiomyocytes, or other electrically active cells expressing optogenetic reporters.

The inverted fluorescence micro-imaging system records optically from numerous (e.g., 50 to 5,000) expressing cells or cell clusters in a single field of view. For example, the system may be used to characterize optically evoked firing patterns and AP waveforms in electrically active cells expressing an Optopatch construct. Each field of view is exposed to whole-field or spatially localized pulses of blue light to evoke activity (e.g., 0.5 s, repeated every 6 s, nine intensities increasing from 0 to 10 mW/cm2 to elicit neuronal firing). The number of steps and power variable depend on the particular study and the expression level of the activator. Reporter fluorescence such as from QuasAr2 may be simultaneously monitored with whole-field excitation at 640 nm, 100 W/cm2. Additional useful discussion of microscopes and imaging systems may be found in U.S. Pat.

No. 8,532,398 to Filkins; U.S. Pat. No. 7,964,853 to Araya; U.S. Pat. No. 7,560,709 to Kimura; U.S. Pat. No. 7,459,333 to Richards; U.S. Pat. No. 6,972,892 to DeSimone; U.S. Pat. No. 6,898,004 to Shimizu; U.S. Pat. No. 6,885,492 to DeSimone; and U.S. Pat. No. 6,243,197 to Schalz, the contents of each of which are incorporated by reference.

Methods of the invention may include exciting the cells that are to be observed or activating a cell to initiate an action potential. Activation may be direct or indirect (e.g., optical activation of an optical activator or activating an upstream cell in gap junction- or synaptically-mediated communication with the cell(s) to be observed). Activation may be optical, electrical, chemical, or by any other suitable method. Activation may involve any pattern of activation including, for example, regular, periodic pulses, single pulses, irregular patterns, or any suitable pattern. Methods may include varying optical activation patterns in space or time to highlight particular aspects of cellular function. For example, a pulse pattern may have an increasing frequency. In certain embodiments, imaging includes activating an electrically active cell that expresses an optical activator using pulses of light.

Figure 11:
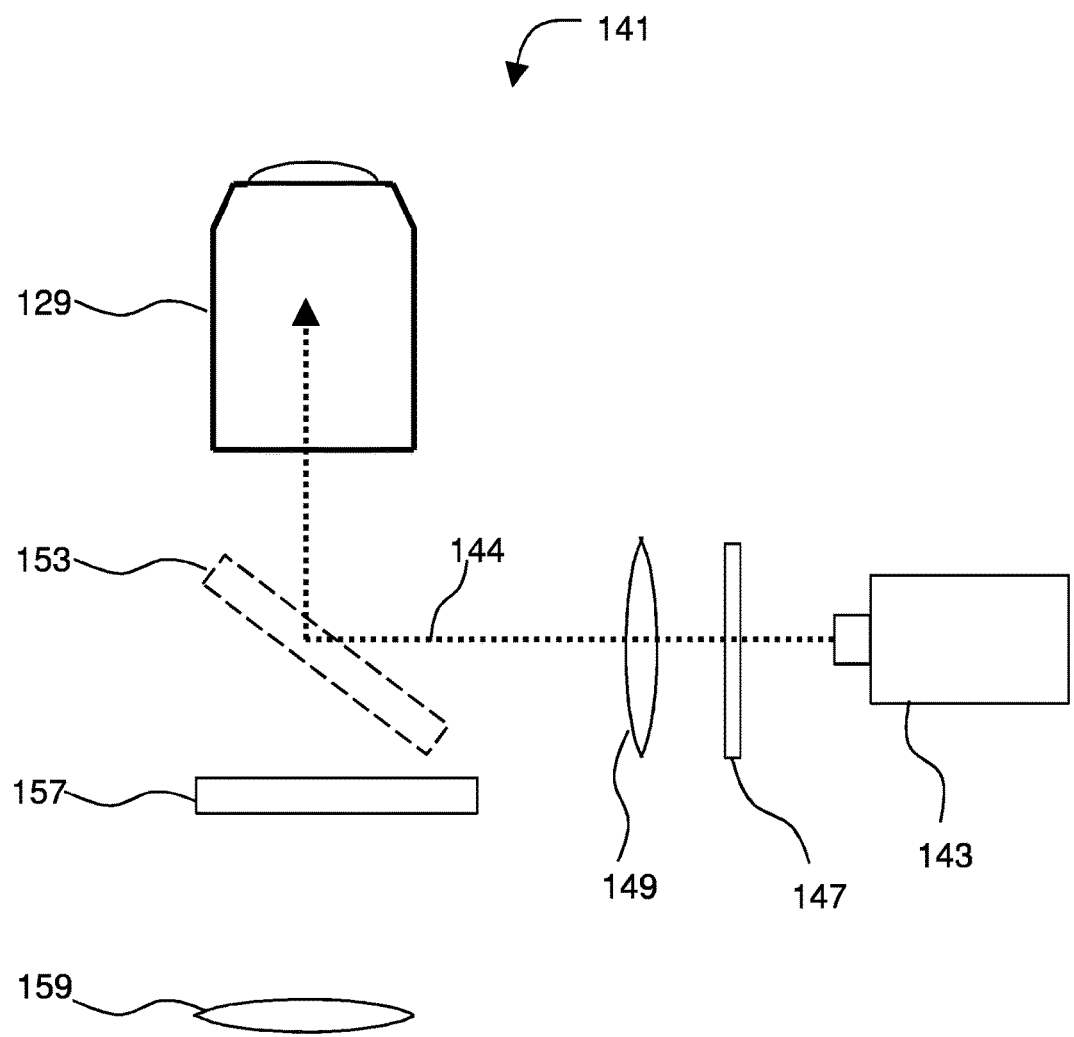
FIG. 11 shows an activation subsystem of the present disclosure.

FIG. 11 shows an activation subsystem 141 according to certain embodiments. The activation subsystem 141 employs a light source 143 (e.g., blue LED) to produce activation light 144 which then passes through a spatial light modulator (SLM) 147 and an activation tube lens 149 before being reflected by a dichroic mirror 153 to pass through the objective unit 129 and impinge upon the sample 113. Microscope 100 preferably includes an optional activation subsystem 141 for exciting light-sensitive compounds in the sample. The illuminator may include one or more light sources 143 and a means for coupling the illumination to the sample. In some embodiments, the illumination can be coupled to the sample from above. In certain embodiments, the system may include an SLM 147 to facilitate selective optical activation of the sample. Light sources 143 may include LEDs, diode lasers, other types of lasers, arc lamps, or other sources with suitable characteristics. Optical filters, mirrors, lenses, prisms, fibers, and other optical elements may be used to alter the spectrum and spatial characteristics of the light source. The SLM may be a digital micromirror device (DMD), liquid crystal display (LCD), or other type of SLM. The SLM may be connected to a computer that controls the illumination pattern, with may be user-defined or it automatically generated by a computer program to correspond to certain features of the sample, such as an individual cell, a group of cells, or a part of a cell. The activation light may be coupled to the sample by a dichroic mirror in the imaging path, a small mirror placed at the back focus of the objective lens, or from above.

The present disclosure provides systems and methods for patterning light onto a sample to separately target activator and reporter cells. In one embodiment cells expressing either activator or reporters are intermixed and co-plated. Cells expressing the activator are identified via a recognizable marker, e.g. a fluorescent protein, or by their absence of fluorescence transients indicating presence of a reporter. This identification is performed through automated image-processing algorithms. Optical activation is achieved by spatially patterning the activation light 144 using a spatial light modulator 147 to project optical activation flashes onto only those cells expressing the activator. The spatial light modulator 147 may be, for example, a DMD, preferably controlled by a computer, may be situated within the illumination path to impart a pattern of light in the illumination path when a laser or light emitting diode (LED) reflects off of it.

Systems of the invention can be used in conjunction with methods involving providing a sample comprising a voltage-indicating or calcium-indicating protein (i.e., an optogenetic reporter) and a light-sensitive moiety (i.e., an optogenetic activator). At least a portion of the sample is illuminated with a first light at a wavelength that causes the light-sensitive moiety to increase ion transport. In certain embodiments, the DLP is connected to a computer device 1035 (FIG. 16) that controls the pattern assumed by the SLM 147. The pattern can be user-defined, or it can be defined by a computer to correspond to a certain region of the sample location, such as an individual cell, a group of cells, or a part of a cell.

The computer device 1035 connected to the DLP will typically include a processor coupled to memory and one or more input/output device. Suitable I/O devices include monitor, keyboard, mouse, pointer, trackpad, touchscreen, camera, Wi-Fi card, network interface card, USB port, others, and combinations thereof. In certain embodiments, computer 1035 includes a touchscreen. The touchscreen may be configured to display a real-time image captured by the objective lens. The touchscreen can be operable to accept user inputs comprising touching the touchscreen. In some embodiments, the touchscreen can be manually controlled by a user to activate a certain cell displayed on the screen by touching an image of that cell. The touchscreen may be operable to control all aspects of the microscope, including position and tilt angle of the object region, magnification, illumination intensity, illumination wavelength, or any other factor relevant to the use and control of a fluorescence microscope that would be known to those of ordinary skill in the art.

The touchscreen controls can include turning a laser bar on or off; changing the configuration of the SLM by selecting certain regions of the image to be illuminated or de-illuminated; or changing a wavelength of an illumination path. The touchscreen can be configured to accept user inputs based on the user touching an area of the image corresponding to a particular area in the sample (e.g., a particular cell) that the user wants to activate or deactivate.

Figure 12:
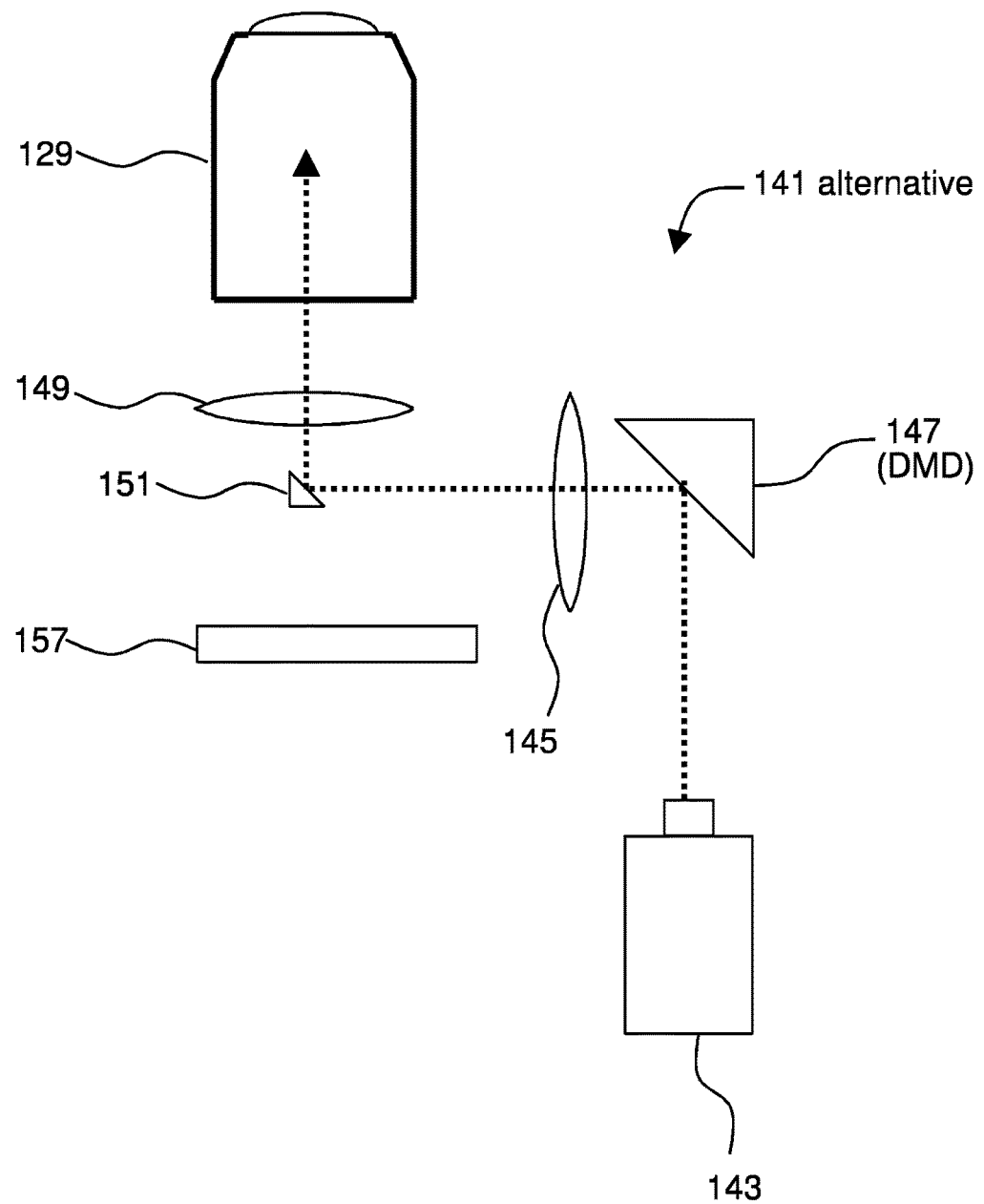
FIG. 12 shows another embodiment of an activation subsystem of the present disclosure.

FIG. 12 depicts an alternative embodiment for an activation subsystem 141 according to certain embodiments. The activation subsystem 141 employs a light source 143 (e.g., blue LED) to produce activation light 144 which then is patterned by the SLM 147. Lenses 145 and 149 create an infinity space within which a mirror 151 passes the activation light into the objective unit 129 to impinge upon the sample 113.

Microscope 100 provides a large FOV, high-resolution imaging system. The microscope 100 may include features such as objective, emission filter, tube lens, and image detector. In some embodiments, the image detector is an sCMOS camera. The illumination subsystem 131 may include one or more of a light source (e.g., diode laser bar), beam shaping and aiming optics, coupling to sample, others, or combinations thereof. Preferably the angle of illumination is slightly less than the TIR angle.

Where the light source is a diode laser bar, there may be a cylindrical lens placed at its focal length from the source with its curved axis parallel to the fast axis of the laser beam.

FIGS. 13A-13C show various views of a prism 125 for use with the present disclosure. As discussed above, microscope systems of the invention include a prism coupled to the sample region, whereby the prism is configured to impart near-total internal reflection on an illumination beam. As would be understood by a person of ordinary skill in the art of optics, near-TIR results in only a thin region of sample being illuminated (i.e., the region of sample in contact with the prism).

FIGS. 13A-13C show the geometry of an embodiment of prism 125 in detail. The prism geometry can be adapted based on the type of different sample container. The prism may have a substantially cuboid shape. It may have a bevel on a bottom edge. It may have a bottom surface that is curved in the shape of a sphere or an asphere. A surface of the prism may be treated with an optical coating to increase the transmission of a fluorescent emission. As shown in FIG. 13A, the prism may have a generally trapezoidal cross-section with beveled edges 801 on faces 803 and 804. FIG. 13B shows a perspective view of the prism 800. FIG. 13C shows a head-on view of the wider face 802, which in embodiments may be configured to be in contact with the object region or with an index matching fluid. As shown in FIG. 13A, faces 803 and 804 are defined by angle 808 with respect to face 802. The angle 808 contributes to a resulting bend in an illumination path that passes through faces 803 and 804. In various embodiments an illumination path (not shown) may pass through faces 803, 804, or 805 such that the prism causes the illumination path to achieve near-TIR with respect to a glass coverslip or other medium supporting the sample.

Figure 14A:
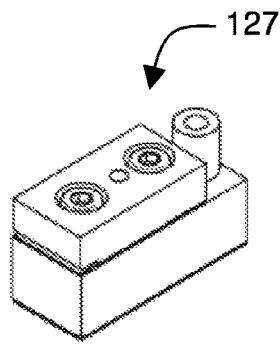
FIGS. 14A-14C show an illumination light source suitable for use with the present disclosure.
Figure 14B:
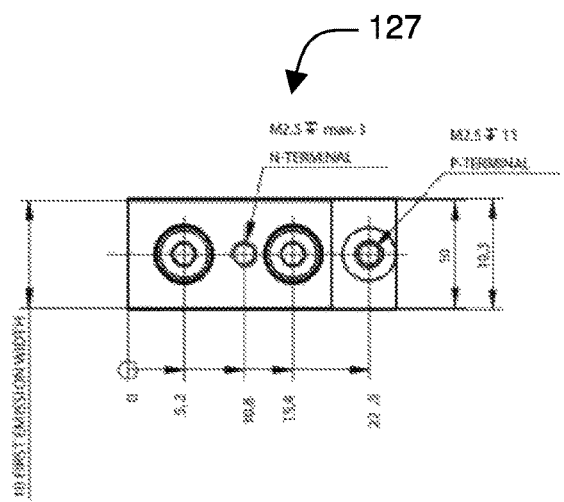
Figure 14C:
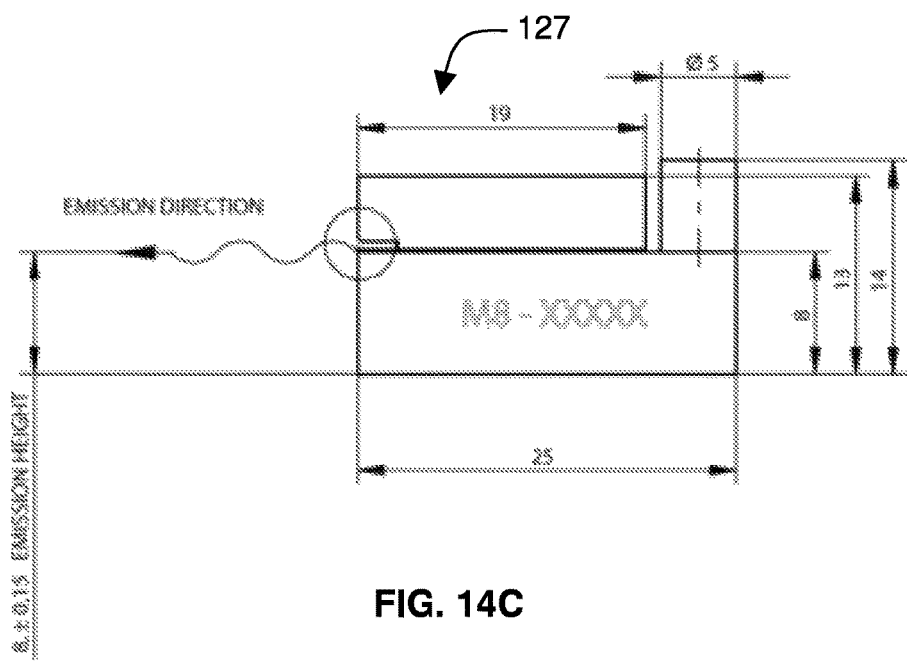

FIGS. 14A-14C show an example of an illumination light source 127 suitable for use with the invention. Light sources may include diode lasers, diode bar lasers, other types of lasers, LEDs, or other light sources with suitable characteristics.

Figure 15:
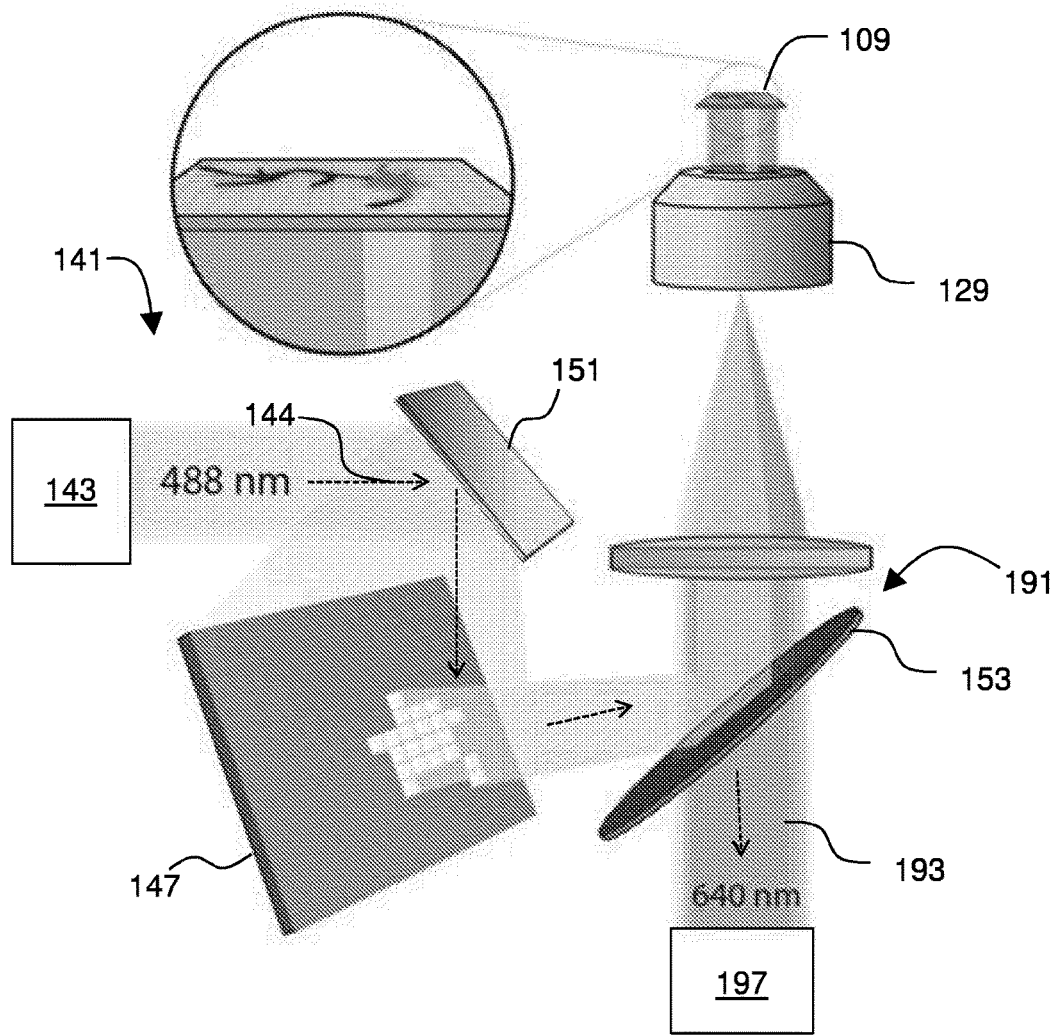
FIG. 15 shows providing patterned illumination while taking an image of the sample

FIG. 15 shows a schematic diagram of providing patterned illumination while taking an image of the sample. A 488 nm blue laser beam 144 from light source 143 is reflected off a spatial light modulator 147 such as a DMD. The DMD imparts a spatial pattern on the blue laser beam (used for CheRiff excitation) before reflecting off a dichroic mirror 153 on its way to the object region via the objective unit 129. The micromirrors are re-imaged onto the sample supported by sample stage 109, leading to an arbitrary user-defined spatio-temporal pattern of illumination at the sample. Simultaneous whole-field illumination with 640 nm red light from the illumination subsystem (not shown) excites fluorescence of the reporter. Imaging light 193 travels down through the objective 129 and the dichroic mirror 153 to the image sensor 197.

Figure 16:
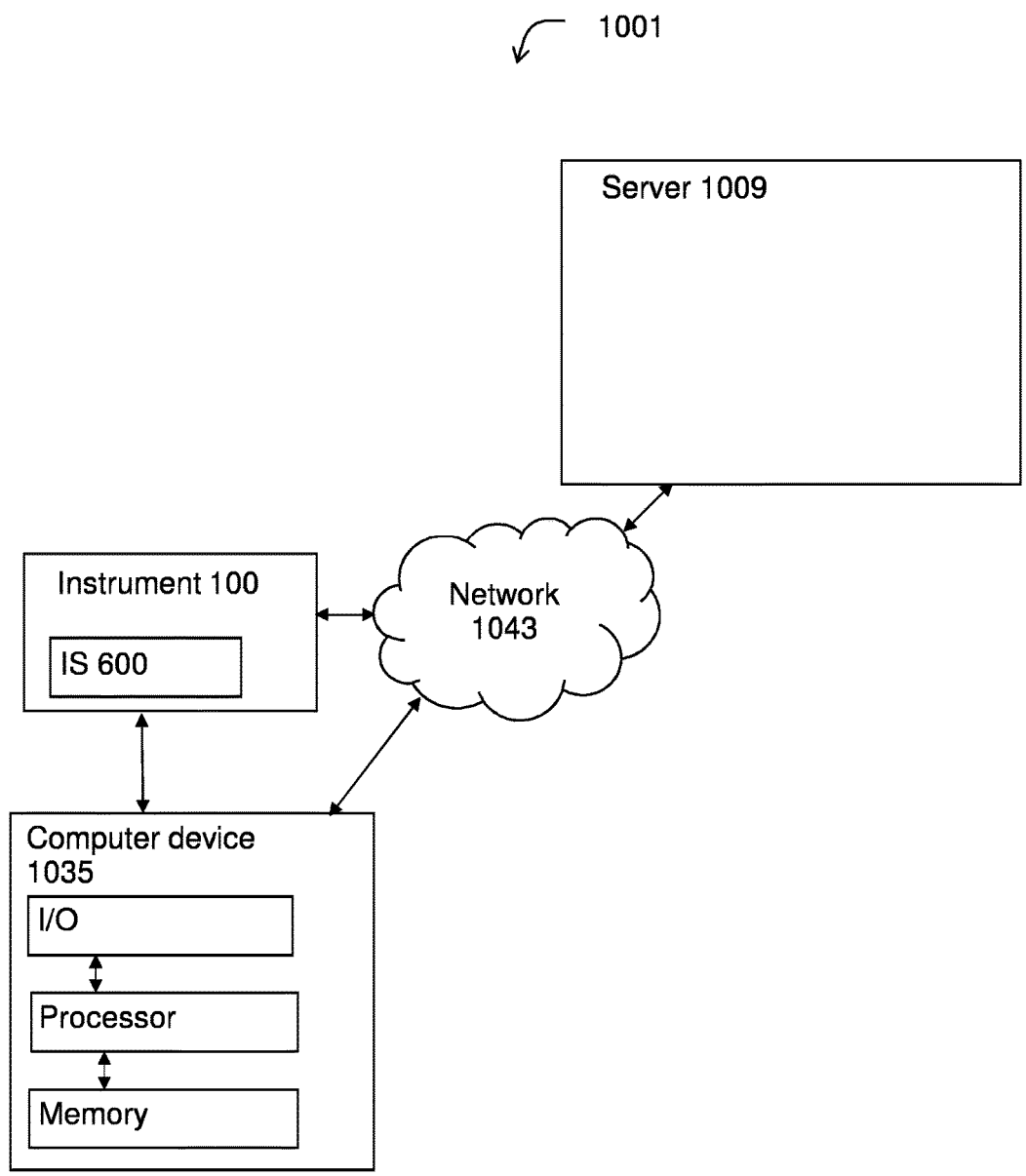
FIG. 16 shows a system for control and use of microscopy instrument.

FIG. 16 diagrams a system 1001 for control and use of microscopy instrument 100. Instrument 100 includes optical system 600 and is connected directly or via network 1043 to computer device 1035. Optionally, system 1001 may include or access a server computer 1009. The system 1001 provides fluorescence microscopy for optogenetics. The system includes an instrument 100 and a computer 1035. The instrument 100 preferably includes an object region defining a sample location and an objective lens located in an imaging optical path that includes the object region. The instrument 100 may include one or more prisms for total internal reflection microscopy; one or more laser bars to provide light; and a digital light processor (DLP) comprising a digital micromirror device. Computer device 1035 includes a touchscreen configured to display an image captured via the objective lens and to control a pattern of activation light based on user input obtained via the touchscreen. Using system 1001, a user may touch the touchscreen to activate an electrically active cell displayed on the touchscreen. The computer 1035 and the DLP can alter a configuration of the digital micromirror device in response to the user touching the touchscreen. Additionally or alternatively, a microscope stage can respond to pan or zoom gestures made by the user using the touchscreen. For example, the user can touch the screen to adjust a position of the object region relative to the objective.

In certain aspects, the present disclosure provides a high-resolution, large field of view imaging system. The imaging system may include an objective lens, a tube lens, optical filters, mirrors, a focusing mechanism, and other optical elements to form an image in an image plane. The imaging system may also include an image detector that resides in the image plane of the imaging system for recording fluorescence images of the sample.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

FIGS. 17-29 show data recorded with a microscope of the invention.

For FIGS. 17-20, the microscope was used to image rat hippocampal neurons.

FIG. 17 is an image of QuasAr in rat hippocampal neurons illuminated (QuasAr3). FIG. 18 is a white light image of rat hippocampal neurons.

Figure 19:
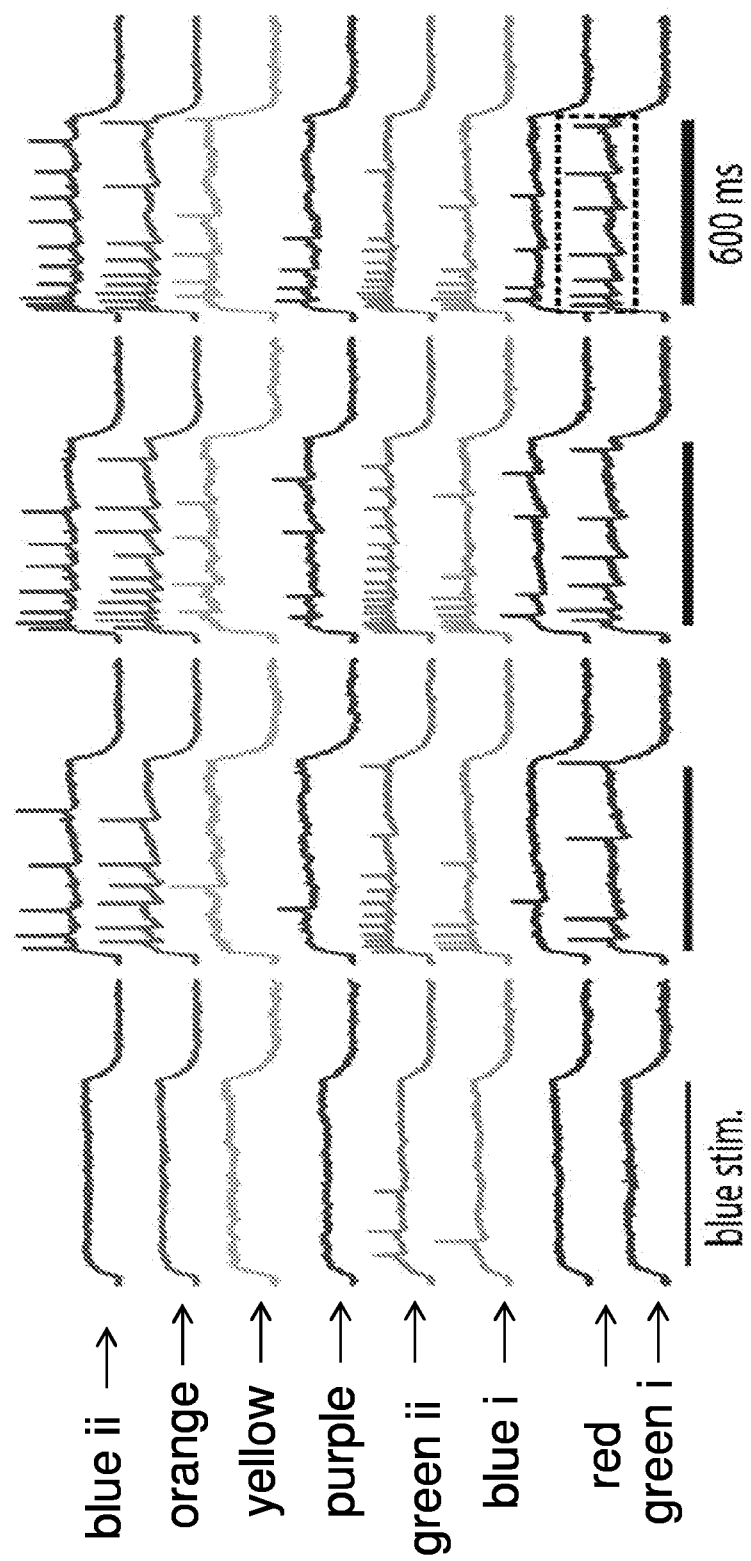
FIG. 19 shows traces from the rat hippocampal neurons.

FIG. 19 shows example traces from the rat hippocampal neurons generated by the QuasAr reporters. The color word labels are included to correlate specific traces to specific neurons surrounding by correspondingly labelled boxes in FIGS. 17 and 18.

Figure 20:
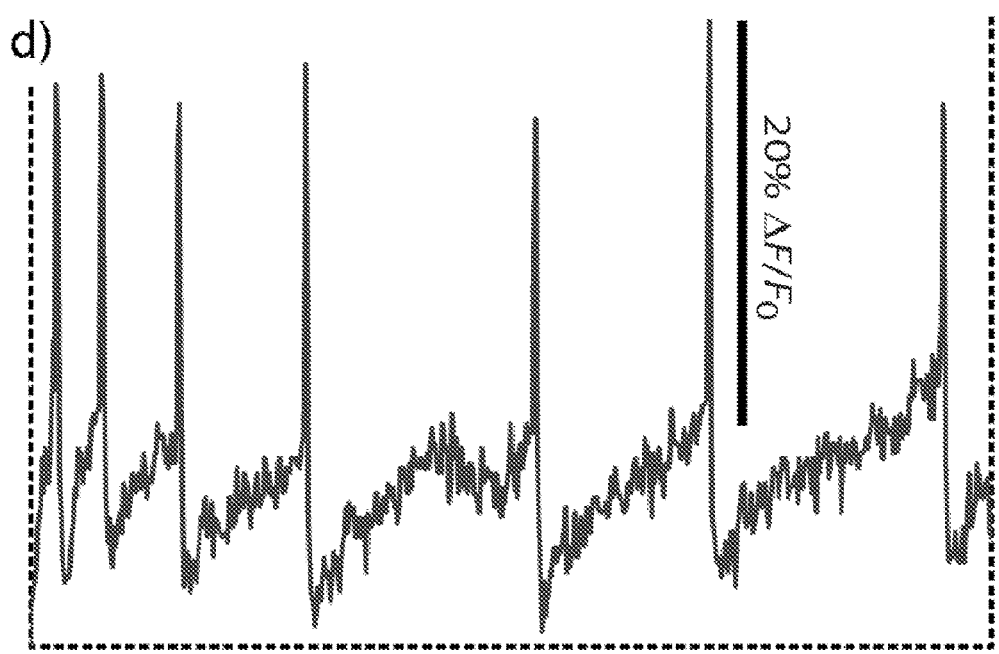
FIG. 20 is a zoomed-in view of the one epoch called out via a dashed-line box in FIG. 19.

FIG. 20 is a zoomed-in view of the one epoch called out via a dashed-line box in FIG. 19.

FIGS. 21-24 result from imaging mouse dorsal root ganglions (DRG) through fused silica and glass coverslips.

Figure 21:
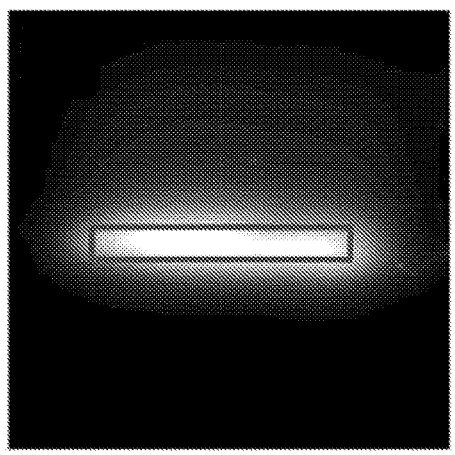
FIG. 21 is an image of a glass coverslip.

FIG. 21 is an image of a glass coverslip.

Figure 22:
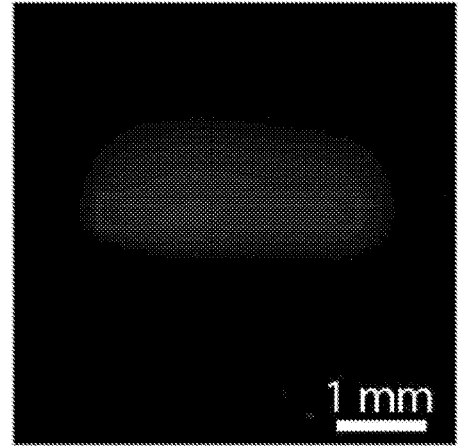
FIG. 22 is an image of a fused silica coverslip.

FIG. 22 is an image of a fused silica coverslip.

Figure 23:
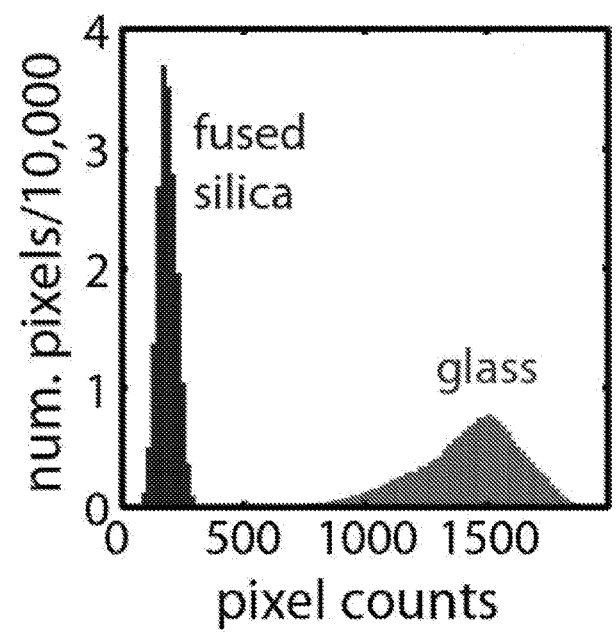
FIG. 23 gives relative pixel counts for fused silica versus glass coverslip.

FIG. 23 gives relative pixel counts under identical illumination conditions for fused silica versus glass coverslip.

Figure 24:
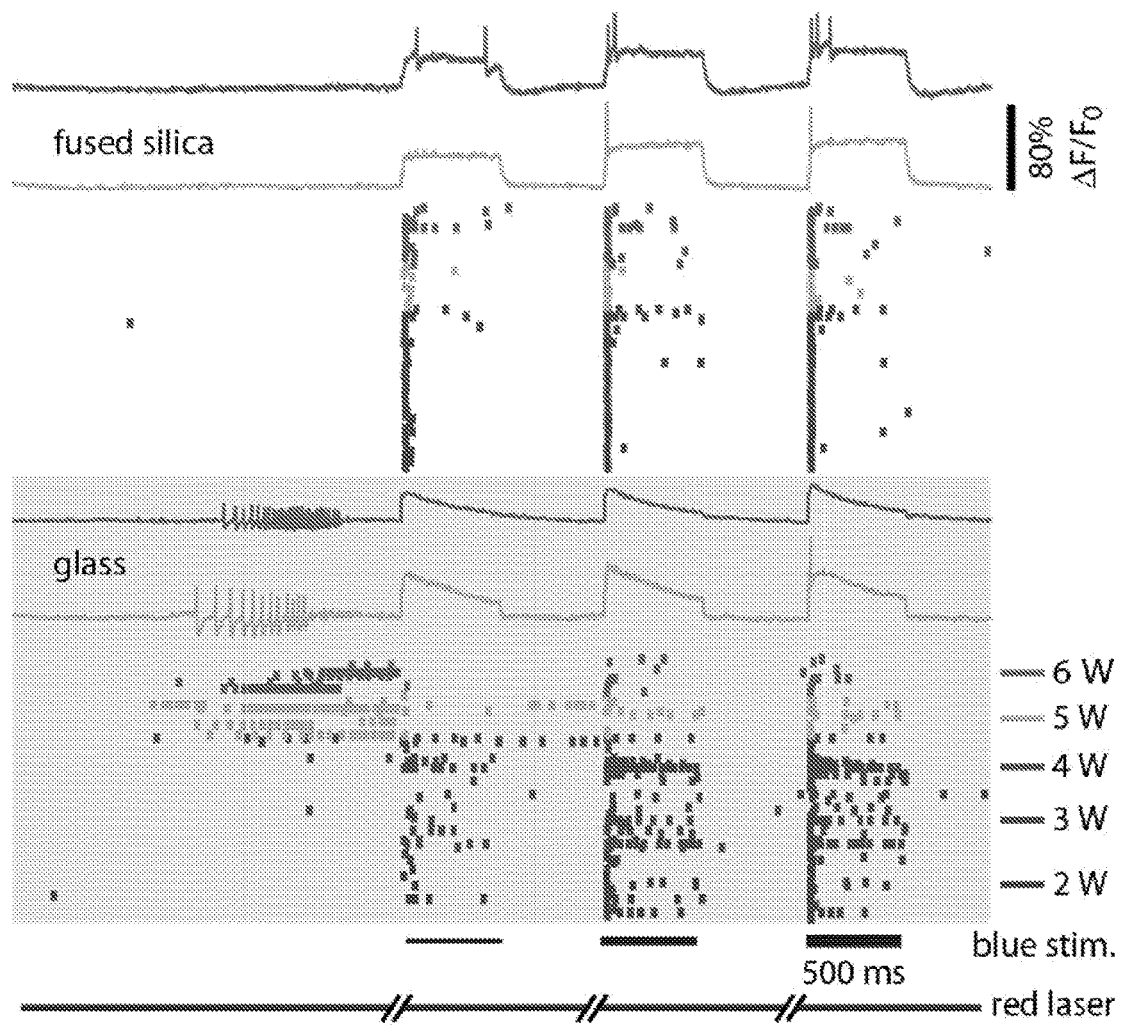
FIG. 24 shows recordings from mouse DRG neurons on fused silica and glass.

FIG. 24 presents recordings of mouse DRG neurons on fused silica and glass and raster plots for each as the laser intensity is increased.

Figure 25:
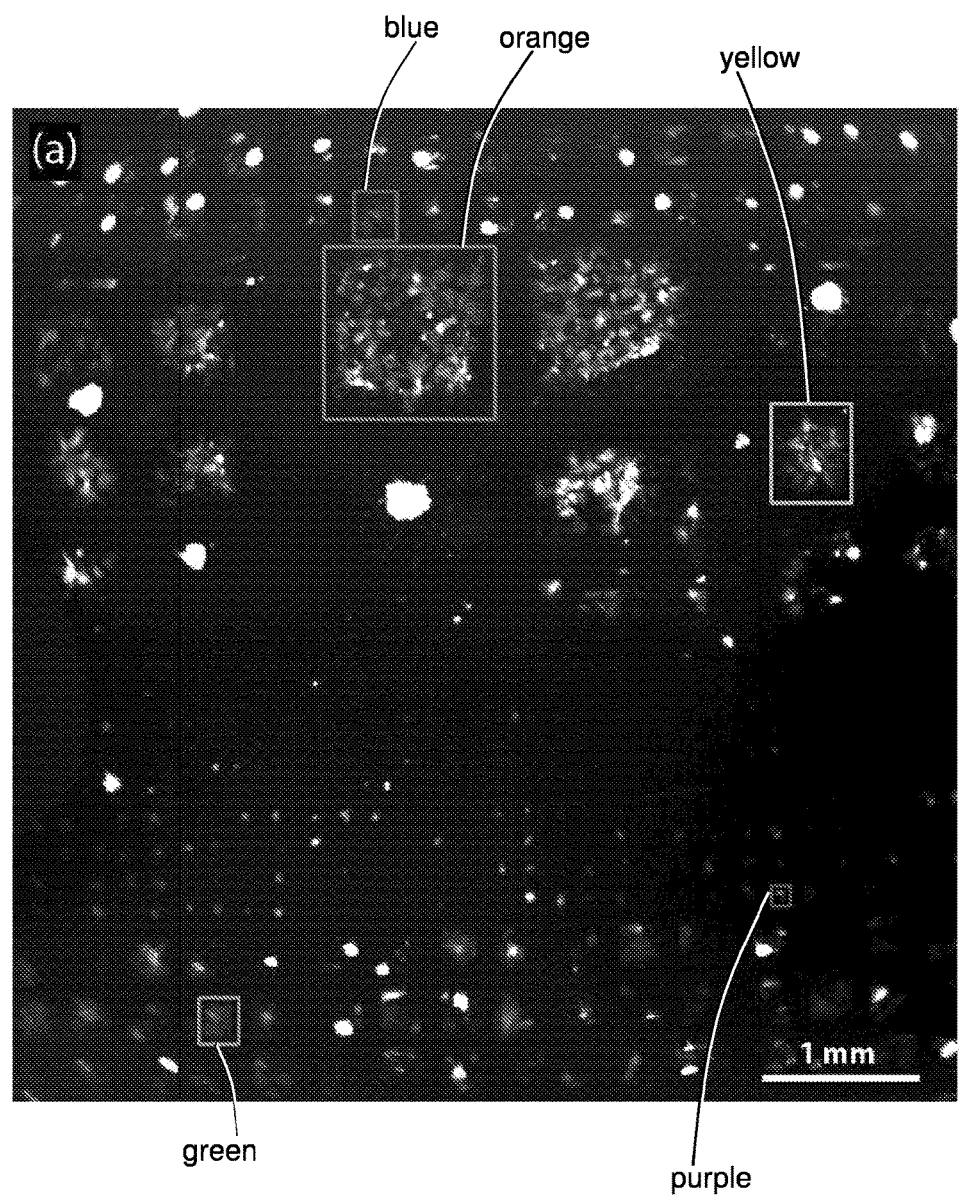
FIG. 25 is a GCaMP6F image from cardiac cells.

FIGS. 25-29 show results from cardiac recording. FIG. 25 is a GCaMP6F image. Boxes have been labeled with color words for ease of cross-referencing to traces in FIG. 26.

Figure 26:
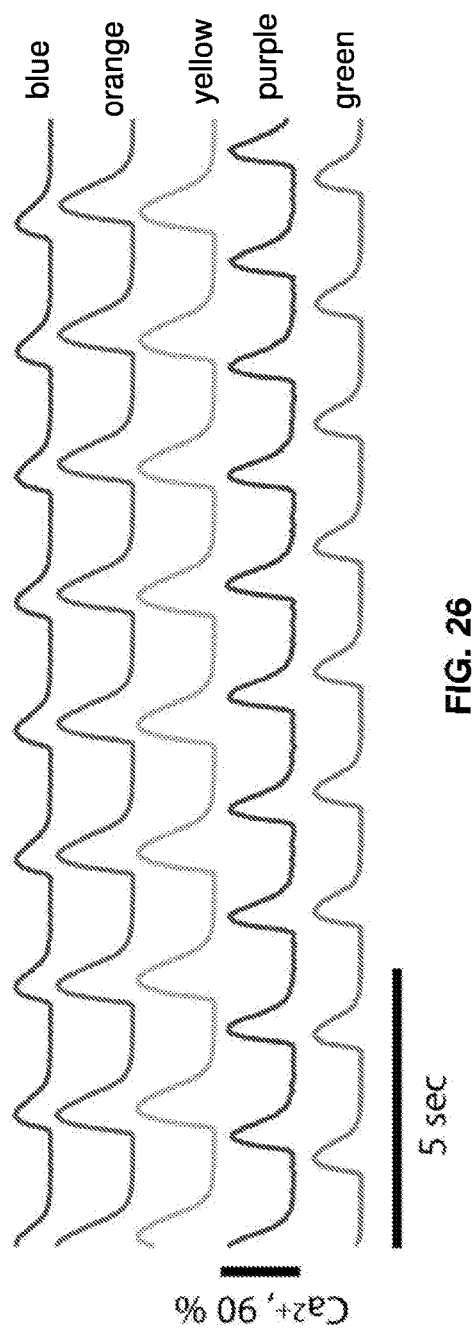
FIG. 26 shows recordings from the boxes in FIG. 25.

FIG. 26 shows recordings from the boxes in FIG. 25.

Figure 27:
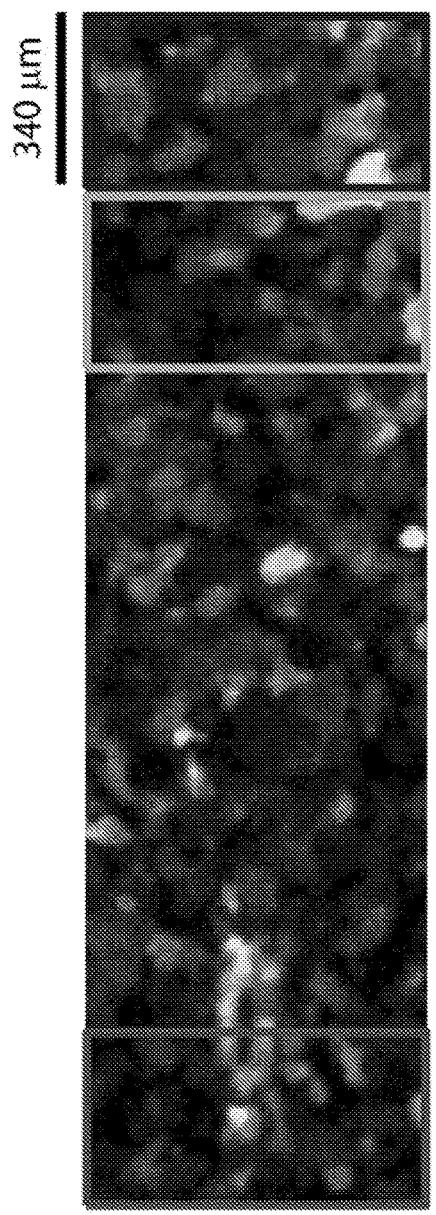
FIG. 27 is an image of cardiac cells co-transfected with CheRiff and QuasAr2.

FIG. 27 is an image of cardiac cells co-transfected with CheRiff and QuasAr2.

Figure 28:
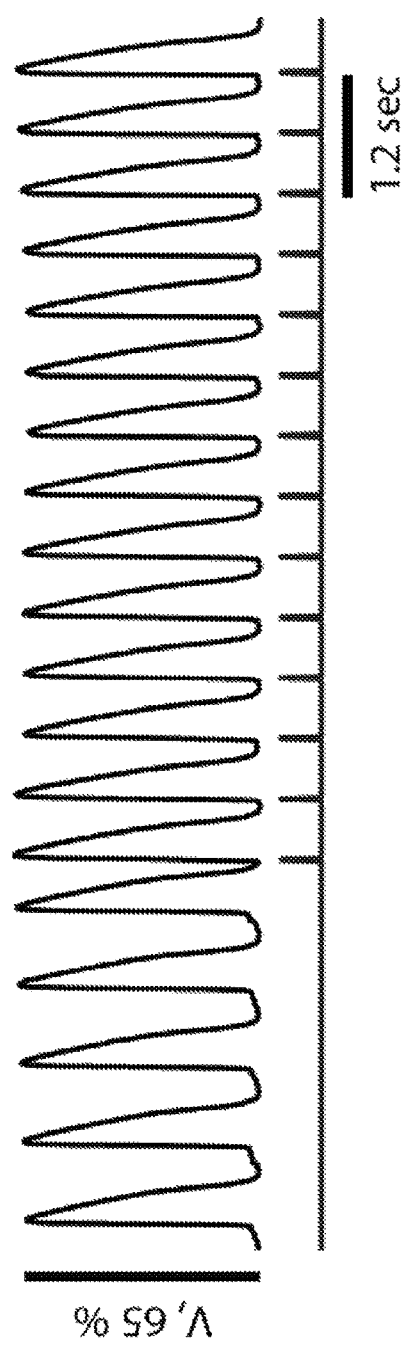
FIG. 28 is a cardiac trace showing spontaneous and paced activity.

FIG. 28 is a cardiac trace showing spontaneous and paced activity.

Figure 29:
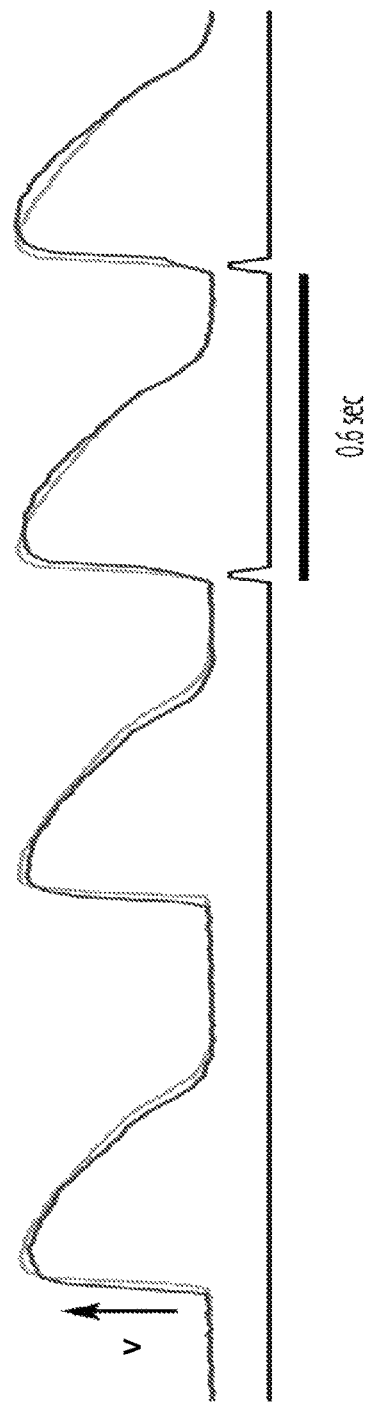
FIG. 29 shows cardiac wave propagation.

FIG. 29 shows wave propagation from left to right during spontaneous, and from right to left during pacing.

What is claimed is:

1. A near-total internal reflection fluorescence microscope comprising:
a stage comprising an object region configured to support a sample;
an illumination subsystem comprising a prism disposed beneath the object region, the prism comprising an upper surface proximal to the object region, a lower surface distal to the object region, and at least one side surface adjoining the upper surface and the lower surface, and a light source operable to transmit light onto the at least one side surface of the prism without achieving total internal reflection when the sample is on the stage, causing the prism to illuminate the sample from beneath by near-total internal reflection; and
an imaging subsystem comprising an objective lens unit disposed beneath the prism and an image capture device operable to receive an image passed through the objective lens unit from the object region.

2. The microscope of claim 1, wherein the object region supports the sample by means of a sample dish with a transparent bottom portion.

3. The microscope of claim 2, wherein the prism and transparent bottom portion are coupled by a low-autofluorescence index matching fluid; and wherein the prism, the index matching fluid, and the transparent bottom portion have a common index of refraction.

4. The microscope of claim 2, wherein the sample dish can hold an aqueous medium and provide access to the sample from above.

5. The microscope of claim 4, further comprising an environmental control subsystem operable to control one or more of humidity, temperature, and gas of the sample region above the aqueous medium to maintain living cells in the aqueous medium.

6. The microscope of claim 1, further comprising an activation subsystem comprising an activation light source configured to transmit activation light that is spectrally distinct from the illumination light onto the sample.

7. The microscope of claim 6, wherein the activation light source and the light source are each selected from the group consisting of: a laser, a diode laser bar; a diode laser; and an LED.

8. The microscope of claim 6, wherein the activation subsystem transmits the activation light upwards through the objective lens unit and onto the sample.

9. The microscope of claim 6, further comprising an activation tube lens disposed within a path defined by the activation light, operable to focus the activation light at a back aperture of the objective lens.

10. The microscope of claim 6, wherein the activation subsystem comprises a spatial light modulator operable to spatially pattern the activation light onto the sample, wherein the spatial light modulator comprises one selected from the group consisting of: a digital micromirror device; a digital light processor; and a liquid crystal display.

11. The microscope of claim 10, wherein the spatial light modulator is controlled by a computer operable to define an illumination pattern.

12. The microscope of claim 11, wherein the illumination pattern is generated by the computer based on an input from the imaging subsystem, wherein the input from the imaging subsystem comprises a pattern of one or more cells in the sample.

13. The microscope of claim 12, wherein the computer defines an illumination pattern with the spatial light modulator that corresponds to the pattern of cells in the sample, thereby causing the activation subsystem to transmit illumination light onto the one or more cells.

14. The microscope of claim 6, further comprising a dichroic mirror to reflect the activation light upwards onto the sample, and to allow the image to pass downward through to the image capture device.

15. The microscope of claim 6, wherein the activation light has a wavelength between 450 and 495 nm, an intensity of about 22 mW/cm2, or both.

16. The microscope of claim 1, wherein the illumination light has a wavelength between 580 and 650 nm, an intensity of about 100 W/cm2, or both capable of illuminating a microbial rhodopsin.

17. The microscope of claim 1, further comprising baffles positioned to prevent unwanted reflected light from entering the objecting lens.

18. The microscope of claim 1, further comprising other beam shaping optics disposed within a path defined by the illumination light, operable to shape the illumination light.

19. The microscope of claim 1, wherein the objective lens has a numerical aperture between 0.4 and 1.0.

20. The microscope of claim 1, wherein the objective lens has a numerical aperture of about 0.5.

* * * * *